(12) United States Patent
Ochs et al.

(10) Patent No.: US 7,700,196 B2
(45) Date of Patent: Apr. 20, 2010

(54) METHOD FOR PRODUCING CARBONYL GROUP-CONTAINING ORGANOSILICON COMPOUNDS

(75) Inventors: Christian Ochs, Burghausen (DE); Elke Fritz-Langhals, Ottobrunn (DE)

(73) Assignee: Wacker Chemie AG, Munich (DE)

( * ) Notice: Subject to any disclaimer, the term of this patent is extended or adjusted under 35 U.S.C. 154(b) by 1003 days.

(21) Appl. No.: 10/595,955

(22) PCT Filed: Nov. 18, 2004

(86) PCT No.: PCT/EP2004/013137

§ 371 (c)(1),
(2), (4) Date: May 22, 2006

(87) PCT Pub. No.: WO2005/049697

PCT Pub. Date: Jun. 2, 2005

(65) Prior Publication Data
US 2007/0129520 A1 Jun. 7, 2007

(30) Foreign Application Priority Data
Nov. 20, 2003 (DE) ................ 103 54 259

(51) Int. Cl.
*C08F 6/00* (2006.01)
(52) U.S. Cl. .................. 428/492; 528/489; 528/24
(58) Field of Classification Search .............. 528/24, 528/489, 492
See application file for complete search history.

(56) References Cited

U.S. PATENT DOCUMENTS

| | | |
|---|---|---|
| 2,803,637 A | 8/1957 | Speier |
| 2,947,770 A | 8/1960 | Snyder et al. |
| 2,970,150 A | 1/1961 | Snyder |
| 5,021,601 A | 6/1991 | Frances et al. |
| 5,739,246 A | 4/1998 | Graiver et al. |
| 6,121,404 A | 9/2000 | Liles |
| 2003/0073871 A1 | 4/2003 | Fritz-Langhals et al. |

FOREIGN PATENT DOCUMENTS

| | | |
|---|---|---|
| DE | 36 32 869 | 3/1988 |
| EP | 0 392 948 | 10/1990 |
| EP | 0 402 274 | 12/1990 |
| EP | 0 612 759 | 10/1996 |
| EP | 1 302 456 | 4/2003 |
| FR | 1 224 081 | 6/1960 |
| JP | 2001-163818 A | 6/2001 |
| JP | 2002-020323 A | 1/2002 |
| JP | 2003-073332 A | 3/2003 |
| WO | 9957158 A1 | 11/1999 |

OTHER PUBLICATIONS

English Abstract corresponding to JP 2001-163818 A.
English Abstract corresponding to JP 2002-020323 A.
English Abstract corresponding to JP 2003-073332 A.
Ullmann's Encyclopedia of Industrial Chemistry, vol . B2, 5$^{th}$ Ediction, VCH Weinheim, 1988, pp. 24-1 to 25-13 & 25-19 to 25-21.
Ullmann's Encyclopedia of Industrial Chemistry, vol. B4, 5$^{th}$ Edition, VCH Weinheim, 1992, pp. 591-586.
Ullmann's Encyclopedia of Industrial Chemistry, vol. B4, 5$^{th}$ Edition, VCH Weinheim, 1992, pp. 87-120.
Committee of the International Union of Biochemistry and Molecular Biology, Enzyme Nomenclature, Academic Press, Inc. 1992, pp. 24-154.
English Derwent Abstract AN 2003-450891 [43] corres. to EP 1 302 456 A1.
English Derwent Abstract AN 1990-314604 [42] corres. to EP 0 392 948.
English Derwent Abstract AN 1990-370275 [50] corres. to EP 0 402 274.
English Derwent Abstract AN 1988-092561 [14] corres. to DE 3632869.
English Derwent Abstract AN 1994-265900 [33] corres. to EP 0612759.
English Derwent Abstract AN 1969-450207 corres. to FR 1531637.

*Primary Examiner*—Kuo-Liang Peng
(74) *Attorney, Agent, or Firm*—Brooks Kushman P.C.

(57) ABSTRACT

Organosilicon compounds bearing keto or aldehyde groups are easily prepared in high yield by oxidation of a carbinol-functional precursor by an oxidizing agent in the presence of a nitrogen-containing free radical mediator which contains aliphatic, cycloaliphatic, heterocyclic, or aromatic NO—, NOH—, or H—N—OH group. The oxidation may be conventional, i.e. using air, oxygen, or other oxidant, may be electrochemical, or enzymatic.

21 Claims, No Drawings

METHOD FOR PRODUCING CARBONYL GROUP-CONTAINING ORGANOSILICON COMPOUNDS

CROSS-REFERENCE TO RELATED APPLICATION

This application is the U.S. national phase of PCT Appln. No. PCT/EP2004/013137 filed Nov. 18, 2004, which claims priority to German application 103 54 259.0 filed Nov. 20, 2003.

BACKGROUND OF THE INVENTION

1. Field of the Invention

The invention relates to a method for producing organosilicon compounds having carbonyl radicals, and the use thereof.

2. Description of the Related Art

Aldehydes and ketones are widely used in organic chemistry and are important precursors in the synthesis of, for example, heterocycles, fragrances and dyes. In organosilicon chemistry, on the other hand, aldehyde and ketone functions play only a minor role in spite of their extremely interesting reaction profile. The reason for this is the lack of a suitable synthesis route which permits the production of organosilicon compounds having carbonyl radicals in a simple and rapid manner and with high yields.

Only three methods for preparing siloxanes having aldehyde and ketone functionalities are known to date:

FR 1,531,637 A describes the platinum-catalyzed addition reaction of olefins having a blocked aldehyde or ketone function, such as, for example, 1-trimethylsilyloxy-1,3-butadiene, 2-trimethylsilyloxy-4-methyl-1,3-butadiene or 4-trimethylsilyloxy-2-methyl-1,3-butadiene, with hydridofunctional organosilicon compounds and the subsequent hydrolysis step for liberating the carbonyl function. In comparison, FR 1,224,081 A and U.S. Pat. No. 2,803,637 A claim the hydrosilylation of aliphatically unsaturated aldehyde acetals with subsequent, acidic acetal cleavage. Starting materials suitable for this purpose are, for example, acrolein dimethyl acetal, acrolein diethyl acetal, methacrolein diacetate, undecenyl diethyl acetal, octadecenyl diethyl acetal, ketene diethyl acetal, 3-cyclohexene-1-carboxaldehyde diethyl acetal, 5-norbornene-2-carboxaldehyde diethyl acetal or bicyclo[2.2.2]oct-5-ene-2-carboxaldehyde diethyl acetal. Common to the processes is that the desired products are obtainable via a plurality of stages only in moderate yield, in particular the hydrolysis step being tedious and generally extremely problematic owing to the heterogeneous system. In addition, the number of aldehyde or ketone substituents obtainable on an industrial scale in this way is greatly limited by the limited commercial availability of suitable acetals.

According to EP 392 948 A1, EP 402 274 A1 and U.S. Pat. No. 5,021,601 A, polyorganosiloxanes having 1-formylethyl or 2-formylethyl groups are obtainable by hydroformylation of the corresponding vinyl-functional organosilicon compounds. The polysiloxanes which are used as intermediates in DE 36 32 869 A1 and contain tricyclo[5.2.1.0$^{2,6}$] decadiene derivative groups substituted by formyl groups are obtained by basically the same process. A disadvantage of the hydroformylation process is that the conversion of the olefin group takes place only at high pressure and high temperature, and furthermore a quantitative conversion is to be realized only by a very complex procedure. Usually, such sytheses are therefore carried out in an autoclave at a superatmospheric pressure of from 20 to 200 bar and a temperature of 100-150° C. which requires special apparatuses and knowledge about handling the gaseous reactants CO and $H_2$. Moreover, here too the number of aldehyde or ketone substituents obtainable by this method is limited.

U.S. Pat. No. 2,947,770 A and U.S. Pat. No. 5,739,246 A describe a method for preparing carbonyl-functional siloxanes via the ozonolysis of alkenyl-functionalized organosilicon compounds and subsequent reductive cleavage of the ozonide formed. A particular disadvantage of this method is that the ozonolysis of double bonds leads to the degradation of the unsaturated carbon skeleton and hence to a loss of at least one carbon unit.

Furthermore, a large number of by-products formed in the ozonolysis, the costs for producing or handling ozone and the stipulation of a few suitable starting compounds prevent the wide use of this method on the industrial scale.

SUMMARY OF THE INVENTION

It was an object of the invention to provide an economical and selective method for producing organosilicon compounds having carbonyl radicals, by means of which even organosilicon compounds having sensitive aldehyde and ketone groups can be prepared on a large scale, and which meets the continuously increasing requirements in industry with regard to space-time yield and universal applicability. These and other objects are achieved by the present invention, whereby carbinol-functional organosilicon compounds are oxidized in the presence of mediators which contain aliphatic, cycloaliphatic, heterocyclic, or aromatic NO—, NOH—, or

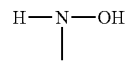

groups.

DETAILED DESCRIPTION OF THE PREFERRED EMBODIMENTS

The invention relates to a method for producing organosilicon compounds having carbonyl radicals by oxidation of an organosilicon compound having carbinol radicals with the aid of a mediator selected from the group consisting of the aliphatic, cycloaliphatic, heterocyclic and aromatic NO—, NOH— or

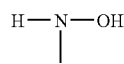

groups, and an oxidizing agent.

In principle, all organosilicon compounds are suitable for the oxidation, provided that they carry primary or secondary carbinol groups.

The organosilicon compounds used in the method according to the invention and having carbinol radicals are preferably compounds containing units of the formula

in which A' may be identical or different and are a radical of the formula

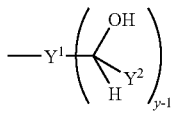 (II)

Y¹ is a divalent or polyvalent, linear or cyclic, branched or straight-chain organic radical which optionally may be substituted and/or interrupted by the atoms N, O, P, B, Si or S, Y² is a hydrogen atom or a monovalent, linear or cyclic, branched or straight-chain, organic radical which optionally may be substituted and/or interrupted by the atoms N, O, P, B, Si or S, y, depending on the valency of radical Y¹, is ≧2, R may be identical or different and are a monovalent, linear or cyclic, branched or straight-chain optionally substituted hydrocarbon radical, X may be identical or different and are a chlorine atom, a radical of the formula —OR¹ where R¹ is a hydrogen atom or alkyl radical having 1 to 18 carbon atom(s), which may be substituted by ether oxygen atoms, a monovalent, linear or cyclic, branched or straight-chain hydrocarbon radical which optionally may be interrupted by units —C(O)—, —C(O)O—, —C(O)NR¹—, —O—C(O)O—, —O—C(O)NR¹—, —NR¹—C(O)—NR¹—, —NR¹—, —(NR¹₂)⁺—, —O—, —S— or =N— and may be substituted by hydroxyl, mercapto, amino, ammonium, carbonyl, carboxyl or oxiranyl groups, or are the group A', a is 0, 1 or 2, preferably 0 or 1, b is 0, 1, 2 or 3, c is 0, 1, 2 or 3, and d is 0, 1, 2 or 3, preferably 0, with the proviso that the sum a+b+c+d is ≦4 and the organosilicon compounds of the formula (I) have at least one radical A' per molecule.

The organosilicon compounds obtained by the method according to the invention and having carbonyl radicals are compounds containing units of the formula

 (III), in which A may be identical or different and are a radical of the formula

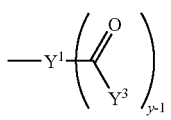 (IV)

Y³ is a hydrogen atom or a monovalent, linear or cyclic, branched or straight-chain organic radical which optionally may be substituted and/or be interrupted by the atoms N, O, P, B, Si or S, and Y¹, R, X, a, b, c, d and y have the meanings stated above therefor, with the proviso that the sum a+b+c+d is ≦4 and the organosilicon compounds of the formula (III) have at least one radical A per molecule.

The organosilicon compounds used or obtained in the method according to the invention may be both silanes, i.e. compounds of the formula (I) where a+b+c+d=4, and siloxanes or siloxane resins, i.e. compounds containing units of the formula (I) where a+b+c+d≦3, in the context of the present invention the term siloxane being intended to include polymeric, oligomeric and dimeric organopolysiloxanes.

Preferably used organosilicon compounds having carbinol radicals are those of the formulae

 (I'),

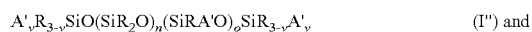 (I'') and

 (I'''), in which A', R and X have the meanings stated above therefor, v is 0, 1, 2 or 3, preferably 0 or 1, w is 0, 1, 2 or 3, n is 0 or an integer from 1 to 2000, o is 0 or an integer from 1 to 2000, preferably from 0 to 500, s may assume a value from 0.2 to 6, preferably from 0.4 to 4, inclusive and describes the number of M units [A'ᵥR₃₋ᵥSiO₁/₂] per Q unit [SiO₄/₂] in the organosilicone resin, with the proviso that they contain at least one radical A' per molecule.

Preferably obtained organosilicon compounds having carbonyl radicals are therefore those of the formula

 (III'),

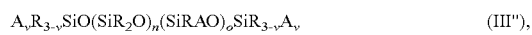 (III''),

 (III''')

in which A, R, X, v, w, n, o and s have the meanings stated above therefor, with the proviso that they contain at least one radical A per molecule.

Examples of radical R are alkyl radicals, such as the methyl, ethyl, n-propyl, isopropyl, 1-n-butyl, 2-n-butyl, isobutyl, tert-butyl, n-pentyl, isopentyl, neopentyl and tert-pentyl radicals; hexyl radicals, such as the n-hexyl radical; heptyl radicals, such as the n-heptyl radical; octyl radicals, such as the n-octyl radical, and isooctyl radicals, such as the 2,2,4-trimethylpentyl radical; nonyl radicals such as the n-nonyl radical; decyl radicals, such as the n-decyl radical; dodecyl radicals, such as the n-dodecyl radical; octadecyl radicals, such as the n-octadecyl radical; cycloalkyl radicals, such as the cyclopentyl, cyclohexyl and cycloheptyl radical and methylcyclohexyl radicals; alkenyl radicals, such as the vinyl, 1-propenyl and 2-propenyl radical; aryl radicals, such as the phenyl, naphthyl, anthryl and phenanthryl radical; alkaryl radicals, such as o-, m- and p-tolyl radicals; xylyl radicals and ethylphenyl radicals; and aralkyl radicals, such as the benzyl radical and the α- and the β-phenylethyl radical.

Examples of substituted radicals R are haloalkyl radicals, such as the 3,3,3-trifluoro-n-propyl radical, the 2,2,2',2',2'-hexafluoroisopropyl radical, and the heptafluoroisopropyl radical, and haloaryl radicals, such as the o-, m- and p-chlorophenyl radical, aminoalkyl radicals, such as the aminopropyl, aminoethylaminopropyl, cyclohexylaminopropyl, dimethylaminopropyl or diethylaminopropyl radical, and acetylated aminoalkyl radicals or aminoalkyl radicals which are alkylated by a Michael-analogous reaction with (meth) acrylic esters, hydroxy-functional radicals, such as those of primary, secondary or tertiary alcohols, such as, for example, the 3-hydroxypropyl and 4-hydroxybutyl radical, or such as the aromatic alcohols, such as, for example, the phenol or eugenol radical, mercapto-functional radicals, such as the 3-mercaptopropyl radical, carboxy-functional radicals and derivatives or salts thereof, such as the acetyl, 3-carboxypropyl, 4-carboxybutyl, 10-carboxydecyl, 3-(2, 5-dioxotetrahydrofuranyl)propyl, 3-(ethane-1,2-dicarboxyl)propyl, 3-acryloyloxypropyl, 3-methacryloyloxypropyl or undecenylsilyl ester radical, epoxy-functional radicals of the group consisting of

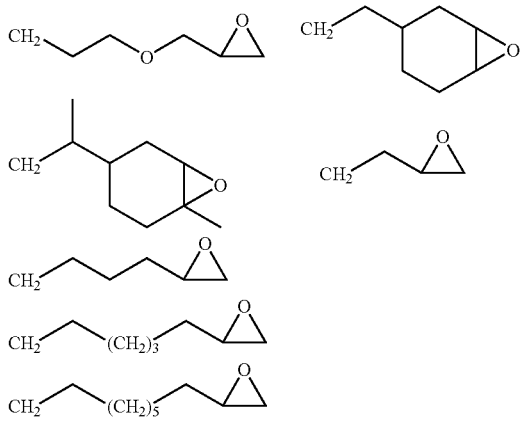

carbonyl-functional radicals, such as the propionaldehyde radical, polyoxyalkylene-functional radicals such as alkylpolyoxyalkylene radicals such as the ethylenepolyoxyalkylene radical and the propylenepolyoxyalkylene radical, phosphonato-functional radicals such as phosphonatoalkyl radicals, silalactone-functional radicals such as glycoside-functional radicals, for example, those in which the glycoside radical, which may be composed of from 1 to 10 monosaccharide units, is linked via an alkylene or oxyalkylene spacer, as disclosed, for example, in EP-B 612 759.

Radicals R are preferably hydrocarbon radicals which have from 1 to 18 carbon atom(s) and are optionally substituted by halogen, hydroxyl, mercapto, amino, ammonium, carboxyl or epoxy groups, the methyl, ethyl, vinyl, n-propyl, n-octyl, n-dodecyl, n-octadecyl and phenyl radicals being particularly preferred.

If the organosilicon compounds according to the invention are organopolysiloxanes, at least 50%, more preferably at least 90%, of all radicals R are methyl or phenyl radicals.

Examples of radicals $R^1$ are the examples stated for radical R. Radical $R^1$ is preferably a hydrogen atom or an alkyl radical having 1 to 8 carbon atom(s), which may be substituted by amino or hydroxyl groups, the hydrogen atom and the methyl, ethyl, propyl and butyl radical being particularly preferred.

Examples of radical X are chlorine atom, the OH group, alkoxy radicals, such as the methoxy, ethoxy, n-propoxy, isopropoxy, 1-butoxy, 2-butoxy, 1-pentyloxy, 1-hexyloxy, 1-octyloxy, 2-octyloxy, isooctyloxy, 1-decyloxy, 1-dodecyloxy, myristyloxy, cetyloxy or stearyloxy radical, quat-functional radicals, such as

—$(CH_2)_3$—$N(CH_3)_3^+$, —$(CH_2)_3$—$\{N(CH_3)_2C_{13}H_{27}\}^+$,

—$(CH_2)_3$—$\{N(CH_3)_2$—$(CH_2)_2$—$N(CH_3)_3\}^{2+}$,
—$(CH_2)_3$—$\{N(CH_2CH_2)_3N\}^+$, —$(CH_2)_3$—NH—$CH_2$—$CH(OH)$—$CH_2$—$N(CH_3)_3^+$,
—$(CH_2)_3$—$N\{CH_2$—$CH(OH)$—$CH_2$—$N(CH_3)_3\}_2^{2+}$,
—$(CH_2)_3$—NH—$(CH_2)_2$—NH—$CH_2$—$CH(OH)$—$CH_2$—$N(CH_3)_3^+$,
—$(CH_2)_3$—[$N\{CH_2$—$CH(OH)$—$CH_2$—$N(CH_3)_3\}$
—$(CH_2)_2$—$N\{CH_2$—$CH(OH)$—$CH_2$—$N(CH_3)_3\}_2]^{3+}$,
—$(CH_2)_3$—NH—$C(O)$—$CH_2$—$N(CH_3)_2C_{18}H_{37}^+$,
—$(CH_2)_3$—O—$CH_2$—$CH(OH)$—$CH_2$—$N(CH_3)_3^+$,
—$(CH_2)_3$—O—$CH_2$—$CH(OH)$—$CH_2$—$N(CH_2CH_3)_3^+$,
—$(CH_2)_{10}$—$C(O)$—NH—$(CH_2)_3$—$N(CH_3)_3^+$,
—$(CH_2)_{10}$—$C(O)$—NH—$(CH_2)_3$—$N(CH_3)_2$—$CH_2$—$C_6H_5^+$,
—$(CH_2)_{10}$—$C(O)$—NH—$(CH_2)_3$—$N(CH_3)_2^+$—$CH_2$—$COO^-$, including the anions necessary for compensating the cationic charge, and the radicals mentioned for radical R.

Radical X is preferably a chlorine atom, the radical A', the radical —$OR^1$ where $R^1$ has the abovementioned meaning, a hydrocarbon radical having 1 to 40 carbon atom(s) which may optionally be interrupted by units —$C(O)$—, —$C(O)O$—, —$C(O)NR^1$—, —O—$C(O)O$—, —O—$C(O)NR^1$—, —$NR^1$—$C(O)$—$NR^1$—, —$NR^1$—, —$(NR^1_2)^+$—, —O—, —S— or =N— and may be substituted by hydroxyl, mercapto, amino, ammonium, carbonyl, carboxyl or oxiranyl groups, or a radical of the general formula $$—R^2—\{[CH_wCH_2O]_e—[C_3H_6O]_f—[(CH_2)_4O]_g—R^3\}_{x-1} \quad (V),$$

in which $R^2$ is a divalent, trivalent or tetravalent organic radical having from 2 to 10 carbon atoms, which may be interrupted by units —O—, —$NR^1$— or —$(NR^1_2)^+$— and is substituted by one or more groups of the formulae

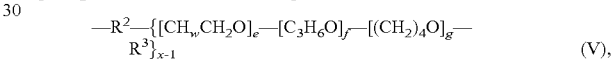

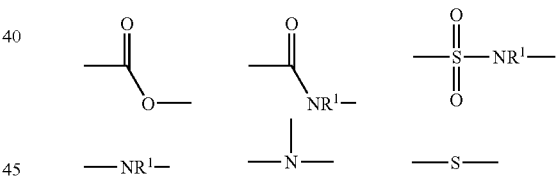

x, depending on the valency of the radical $R^2$, is 2, 3 or 4, $R^3$ is a hydrogen atom or a hydrocarbon radical having 1 to 20 carbon atom(s) which is optionally substituted by a group —$C(O)$—, —$NR^1$—, —$NR^1_2$ or —$(NR^1_2)^+$—, and e, f and g, in each case independently of one another, are 0 or an integer from 1 to 200, with the proviso that the sum e+f+g is ≧1.

Most preferably, radical X is a chlorine atom, a radical A', a hydroxyl radical, a methoxy or ethoxy radical, a vinyl radical, an organic radical having 1 to 18 carbon atom(s) selected from: aliphatic hydrocarbon radicals, aromatic radicals, optionally substituted hydrocarbon radicals, carbinol functional radicals, carboxy- or anhydride-functional radicals, epoxy-functional radicals, amidated amino-functional radicals, and hydrocarbon radicals having a quaternary nitrogen group or a radical of the general formula (V).

Particularly preferably, radicals X are a chlorine atom, radical A', hydroxyl, methoxy or ethoxy radical, vinyl radical, methyl, ethyl, n-propyl, n-octyl, n-dodecyl or n-octadecyl radical, phenyl radical, 2-methyl-2-phenylethyl radical, 3-hydroxypropyl radical, 3-hydroxy-3-methyl-1-butenyl radical 3-(ortho-hydroxyphenyl)propyl radical, eugenol radical, 2-carboxyethyl, 3-carboxypropyl, 4-carboxybutyl, 10-carboxydecyl, 3-(2,5-dioxotetrahydrofuranyl)propyl, 3-(ethane-1,2-dicarboxy)propyl, 3-acryloyloxypropyl, 3-methacryloyloxypropyl or trimethylsilyl undecenoate radical,

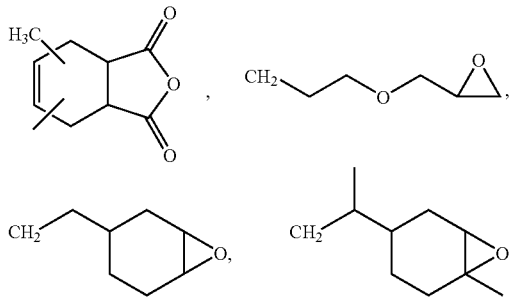

—$(CH_2)_3$—NH—C(O)—$CH_3$, —$(CH_2)_3$—N (cyclo-$C_6H_{11}$)—C(O)—$CH_3$,
—$(CH_2)_3$—N{C(O)—$CH_3$}—$(CH_2)_3$—NH—C(O)—$CH_3$,
or a radical of the general formula (V).
Examples of radical $R^2$ are
—$(CH_2)_2$—O—, —$(CH_2)_3$—O—, —(CH=CH)—$CH_2$—O—,

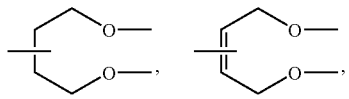

—$(CH_2)_3$—O—$CH_2$—CH(OH)—$CH_2$—O—, —$(CH_2)_3$—O—C(O)—$(CH_2)_2$—NH—,
—$(CH_2)_3$—NH—$CH_2$—CH(OH)—$CH_2$—O—, —$(CH_2)_3$—N{—$CH_2$—CH(OH)—$CH_2$—O—}$_2$,
—$(CH_2)_3$—N (cyclo-$C_6H_{11}$)—$CH_2$—CH(OH)—$CH_2$—O—,
—$(CH_2)_3$—NH—$(CH_2)_3$—NH—$CH_2$—CH(OH)—$CH_2$—O—,
—$(CH_2)_3$—NH—$(CH_2)_3$—N{—$CH_2$—CH(OH)—$CH_2$—O—}$_2$,
—$(CH_2)_3$—N{$CH_2$—CH(OH)—$CH_2$—O—}—$(CH_2)_3$—NH—$CH_2$—CH(OH)—$CH_2$—O—,
—$(CH_2)_3$—N{$CH_2$—CH(OH)—$CH_2$—O—}—$(CH_2)_3$—N{—$CH_2$—CH(OH)—$CH_2$—O—}$_2$,
—$(CH_2)_3$—NH—$CH_2$—C(O)—O—, —$(CH_2)_3$—N{—$CH_2$—C(O)—O—}$_2$,
—$(CH_2)_3$—N (cyclo-$C_6H_{11}$)—$CH_2$—C(O)—O—,
—$(CH_2)_3$—NH—$(CH_2)_3$—NH—$CH_2$—C(O)—O—,
—$(CH_2)_3$—NH—$(CH_2)_3$—N{—$CH_2$—C(O)—O—}$_2$,
—$(CH_2)_3$—N{$CH_2$—C(O)—O—}—$(CH_2)_3$—NH—$CH_2$—C(O)—O—,
—$(CH_2)_3$—N{$CH_2$—C(O)—O—}—$(CH_2)_3$—N{—$CH_2$—C(O)—O—}$_2$,
—$(CH_2)_3$—NH—$CH_2$—C(O)—NH—, —$(CH_2)_3$—N{—$CH_2$—C(O)—NH—}$_2$,
—$(CH_2)_3$—N(cyclo-$C_6H_{11}$)—$CH_2$—C(O)—NH—,
—$(CH_2)_3$—NH—$(CH_2)_3$—NH—$CH_2$—C(O)—NH—,
—$(CH_2)_3$—NH—$(CH_2)_3$—N{—$CH_2$—C(O)—NH—}$_2$,
—$(CH_2)_3$—N{$CH_2$—C(O)—NH—}($CH_2)_3$—NH—$CH_2$—C(O)—NH—,
—$(CH_2)_3$—N{$CH_2$—C(O)—NH—}—$(CH_2)_3$—N{—$CH_2$—C(O)—NH—}$_2$,
—$(CH_2)_3$—NH—$CH_2$—$CH_2$—C(O)—O—, —$(CH_2)_3$—N{—$CH_2$—$CH_2$—C(O)—O—}$_2$,
—$(CH_2)_3$—N (cyclo-$C_6H_{11}$)—$CH_2$—$CH_2$—C(O)—O—,
—$(CH_2)_3$—NH—$CH_2$—CH($CH_3$)—C(O)—O—, —$(CH_2)_3$—N{—$CH_2$—CH($CH_3$)—C(O)—O—}$_2$,
—$(CH_2)_3$—N (cyclo-$C_6H_{11}$)—$CH_2$—CH($CH_3$)—C(O)—O—,
—$(CH_2)_3$—NH—$(CH_2)_3$—NH—$CH_2$—$CH_2$—C(O)—O—,
—$(CH_2)_3$—NH—$(CH_2)_3$—N{—$CH_2$—$CH_2$—C(O)—O—}$_2$,
—$(CH_2)_3$—N{$CH_2$—$CH_2$—C(O)—O—}—$(CH_2)_3$—NH—$CH_2$—$CH_2$—C(C)—O—,
—$(CH_2)_3$—N{$CH_2$—$CH_2$—C(O)—O—}—$(CH_2)_3$—N{—$CH_2$—$CH_2$—C(O)—O—}$_2$,
—$(CH_2)_3$—NH—$(CH_2)_3$—NH—$CH_2$—CH($CH_3$)—C(O)—O—,
—$(CH_2)_3$—NH—$(CH_2)_3$—N{—$CH_2$—CH($CH_3$)—C(O)—O—}$_2$,
—$(CH_2)_3$—N{$CH_2$—CH($CH_3$)—C(O)—O—}—$(CH_2)_3$—NH—$CH_2$—CH($CH_3$)—C(O)—O—,
—$(CH_2)_3$—N{$CH_2$—CH($CH_3$)—C(O)—O—}—$(CH_2)_3$—N{—$CH_2$—CH($CH_3$)—C(O)—O—}$_2$,
—$(CH_2)_3$—NH—$CH_2$—$CH_2$—C(O)—NH—, —$(CH_2)_3$—N{—$CH_2$—$CH_2$—C(O)—NH—}$_2$,
—$(CH_2)_3$—N (cyclo-$C_6H_{11}$)—$CH_2$—$CH_2$—C(O)—NH—,
—$(CH_2)_3$—NH—$CH_2$—CH($CH_3$)—C(O)—NH—,
—$(CH_2)_3$—N{—$CH_2$—CH($CH_3$)—C(O)—NH—}$_2$,
—$(CH_2)_3$—N (cyclo-$C_6H_{11}$)—$CH_2$—CH($CH_3$)—C(O)—NH—,
—$(CH_2)_3$—NH—$(CH_2)_3$—NH—$CH_2$—$CH_2$—C(O)—NH—,
—$(CH_2)_3$—NH—$(CH_2)_3$—N{—$CH_2$—$CH_2$—C(O)—NH—}$_2$,
—$(CH_2)_3$—N{$CH_2$—$CH_2$—C(O)—NH—}—$(CH_2)_3$—NH—$CH_2$—$CH_2$—C(O)—NH—,
—$(CH_2)_3$—N{$CH_2$—$CH_2$—C(O)—NH—}—$(CH_2)_3$—N{—$CH_2$—$CH_2$—C(O)—NH—}$_2$,
—$(CH_2)_3$—NH—$(CH_2)_3$—NH—$CH_2$—CH($CH_3$)—C(O)—NH—,
—$(CH_2)_3$—NH—$(CH_2)_3$—N{—$CH_2$—CH($CH_3$)—C(O)—NH—}$_2$,
—$(CH_2)_3$—N{$CH_2$—CH($CH_3$)—C(O)—NH—}—$(CH_2)_3$—NH—$CH_2$—CH($CH_3$)—C(O)—NH—,
—$(CH_2)_3$—N{$CH_2$—CH($CH_3$)—C(O)—NH—}—$(CH_2)_3$—N{—$CH_2$—CH($CH_3$)—C(O)—NH—}$_2$,
—$(CH_2)_3$—S—$CH_2$—CH(OH)—$CH_2$—O—, —$(CH_2)_3$—S—CH, —$CH_2$—C(O)—O—,
—$(CH_2)_3$—S—$CH_2$—CH($CH_3$)—C(O)—C—,
—$(CH_2)_3$—S—$CH_2$—$CH_2$—C(O)—NH—, —$(CH_2)_3$—S—$CH_2$—CH($CH_3$)—C(O)—NH—,
—$(CH_2)_2$—C(O)O—, —$CH_2$—CH($CH_3$)—C(O)O—,
—$(CH_2)_3$—C(O)O—, —$(CH_2)_{10}$—C(O)O—,
—$(CH_2)_2$—C(O)NH—, —$CH_2$—CH($CH_3$)—C(O)NH—,
—$(CH_2)_3$—C(O)NH—,
—$(CH_2)_{10}$—C(O)NH—,

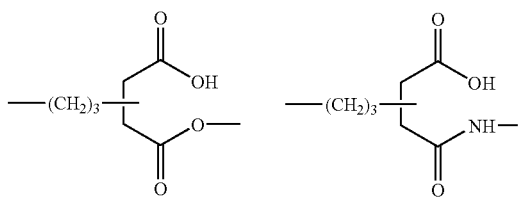

-continued

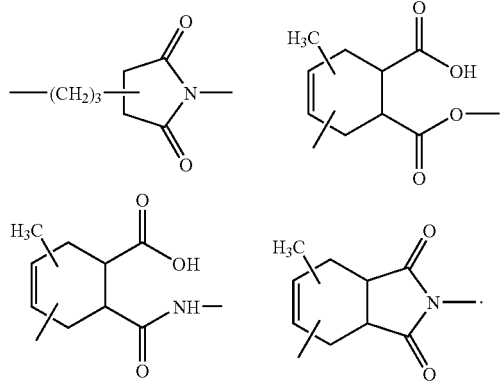

The radical $R^2$ is preferably
—$(CH_2)_2$—O—, —$(CH_2)_3$—O—, —(CH=CH)—$CH_2$—O—,

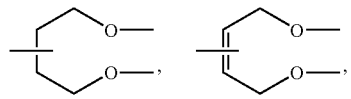

—$(CH_2)_3$—O—$CH_2$—CH(OH)—$CH_2$—O—, —$(CH_2)_3$—S—$CH_2$—CH(OH)—$CH_2$—O—,
—$(CH_2)_3$—NH—$CH_2$—CH(OH)—$CH_2$—O—, —$(CH_2)_3$—N{—$CH_2$—CH(OH)—$CH_2$—O—}$_2$,
—$(CH_2)_3$—NH—$(CH_2)_3$—NH—$CH_2$—CH(OH)—$CH_2$—O—,
—$(CH_2)_3$—NH—$(CH_2)_3$—N{—$CH_2$—CH(OH)—$CH_2$—O—}$_2$,
—$(CH_2)_3$—N{$CH_2$—CH(OH)—$CH_2$—O—}—$(CH_2)_3$—NH—$CH_2$—CH(OH)—$CH_2$—O—,
—$(CH_2)_3$—N{$CH_2$—CH(OH)—$CH_2$—O—}—$(CH_2)_3$—N{—$CH_2$—CH(OH)—$CH_2$—O—}$_2$,
—$(CH_2)_3$—NH—$CH_2$—$CH_2$—C(O)—O—, —$(CH_2)_3$—N{—$CH_2$—$CH_2$—C(O)—O—}$_2$,
—$(CH_2)_3$—NH—$(CH_2)_3$—NH—$CH_2$—$CH_2$—C(O)—O—,
—$(CH_2)_3$—NH—$(CH_2)_3$—N{—$CH_2$—$CH_2$—C(O)—}$_2$,
—$(CH_2)_3$—N{$CH_2$—$CH_2$—C(O)—O—}—$(CH_2)_3$—NH—$CH_2$—$CH_2$—C(O)—O—,
—$(CH_2)_3$—N{$CH_2$—$CH_2$—C(O)—O—}—$(CH_2)_3$—N{—$CH_2$—$CH_2$—C(O)—O—}$_2$,
—$(CH_2)_3$—NH—$CH_2$—$CH_2$—C(O)—NH—, —$(CH_2)_3$—N{—$CH_2$—$CH_2$—C(O)—NH—}$_2$,
—$(CH_2)_3$—NH—$(CH_2)_3$—NH—$CH_2$—$CH_2$—C(O)—NH—,
—$(CH_2)_3$—NH—$(CH_2H)_3$—N {—$CH_2$—$CH_2$—C(O)—NH—}$_2$,
—$(CH_2)_3$—N{$CH_2$—$CH_2$—C(O)—NH—}—$(CH_2)_3$—NH—$CH_2$—$CH_2$—C(O)—NH—,
—$(CH_2)_3$—N{$CH_2$—$CH_2$—C(O)—NH—}—$(CH_2)_3$—N{—$CH_2$—$CH_2$—C(O)—NH—}$_2$,
—$(CH_2)_3$—S—$CH_2$—$CH_2$—C(O)—O—, —$(CH_2)_3$—S—$CH_2$—CH($CH_3$)—C(O)—O—,
—$(CH_2)_2$—C(O)O—, —$CH_2$—CH($CH_3$)—C(O)O—, —$(CH_2)_3$—C(O)O—,
—$(CH_2)_{10}$—C(O)O—,
—$(CH_2)_2$—C(O)NH—, —$CH_2$—CH($CH_3$)—C(O)NH—, —$(CH_2)_3$—C(O)NH—,
—$(CH_2)_{10}$—C(O)NH—,

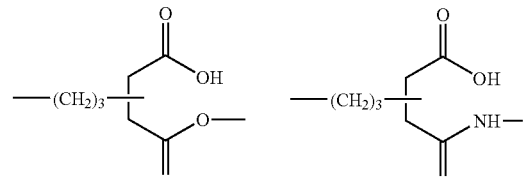

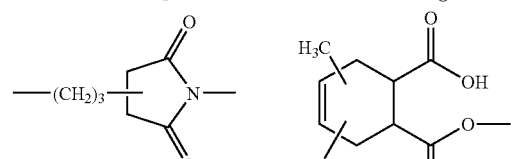

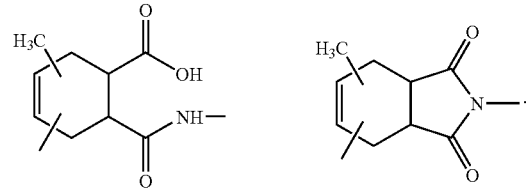

Particularly preferably, radical $R^2$ is
—$(CH_2)_2$—C—, —$(CH_2)_3$—O—, —(CH=CH)—$CH_2$—O—,

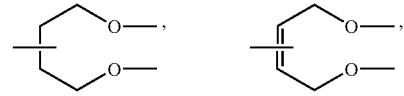

—$(CH_2)_3$—O—$CH_2$—CH(OH)—$CH_2$—O—, —$(CH_2)_3$—S—$CH_2$—CH(OH)—$CH_2$—O—,
—$(CH_2)_2$—C(O)O—, —$CH_2$—CH($CH_3$)—C(O)O—, —$(CH_2)_3$—C(O)O—,
—$(CH_2)_{10}$—C(O)O—,
—$(CH_2)_2$—C(O)NH—, —$CH_2$—CH($CH_3$)—C(O)NH—, —$(CH_2)_3$—C(O)NH—,
—$(CH_2)_{10}$—C(O)NH—,
—$(CH_2)_3$—S—$CH_2$—$CH_2$—C(O)—O—,

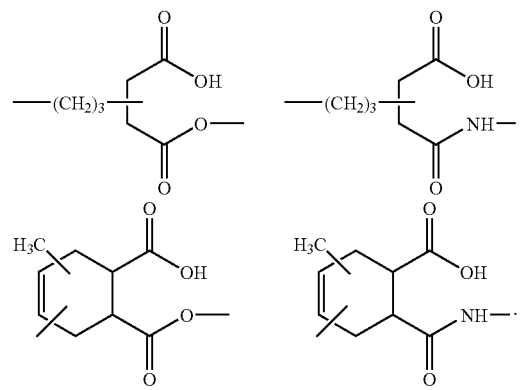

Examples of radical $R^3$ are a hydrogen atom, alkyl radicals, such as the methyl, ethyl, n-propyl, isopropyl, 1-butyl, 1-pentyl, 1-hexyl, 1-octyl, 2-octyl, isooctyl, 1-decyl, 1-dodecyl, myristyl, cetyl or stearyl radical, acyl radicals, such as the formyl, acetyl, acryloyl or methacryloyl radical, or quat-functional radicals such as the radicals

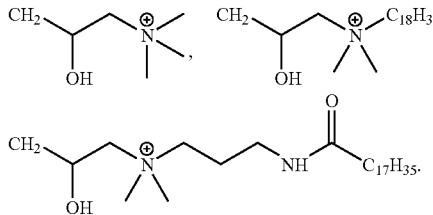

Preferred radicals R³ are a hydrogen atom, the methyl, ethyl, n-propyl, isopropyl, 1-butyl, 1-pentyl, 1-hexyl, 1-octyl, 2-octyl, isooctyl, 1-decyl, 1-dodecyl, myristyl, cetyl or stearyl radical, the formyl, acetyl or acryloyl radical, the hydrogen atom, the methyl radical, the 1-butyl radical, the myristyl, cetyl or stearyl radical and the acetyl or acryloyl radical being particularly preferred.

Examples of radical Y¹ are alkylene radicals such as the methylene, ethylene, propylene, 2-methylpropylene, butylene, pentylene, hexylene, heptylene, octylene, nonylene, undecylene and heptadecylene radical; cyclic and polycyclic alkylene radicals, such as, for example the cyclohexylene, methylcyclohexylene, dimethyl-cyclohexylene and norbornylene radical, unsaturated alkylene radicals, such as the ethenylene, 1-propenylene, 1-butenylene and 2-butenylene radical; ether- and polyether-functional alkylene radicals; esterified and amidated hydroxyalkylene, mercapto-alkylene and aminoalkylene radicals; and alkylene radicals which are interrupted by a carbonic acid derivative group, such as carbonic ester, urethane or urea group.

Radical Y¹ is preferably a divalent or polyvalent, preferably divalent to decavalent, preferably divalent to tetravalent, hydrocarbon radical having 1 to 18 carbon atom(s) which may optionally be interrupted by units —C(O)—, —C(O)O—, —C(O)NR¹—, —O—C(O)O—, —O—C(O)NR¹—, —NR¹—C(O)—NR¹—, —O—, —S— or =N— and may be substituted by hydroxyl, alkoxy, mercaptoalkyl, carbonyl, carboxyl or oxiranyl groups, or a radical of the formula

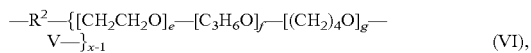

(VI), in which V is a methylene, ethylene, n-propylene or n-butylene radical and in which R², e, f, g and x have the meanings stated above therefor.

Radical Y¹ is particularly preferably the ethylene, propylene, 2-methylpropylene, butylene, pentylene, nonylene and undecylene radical, the radicals

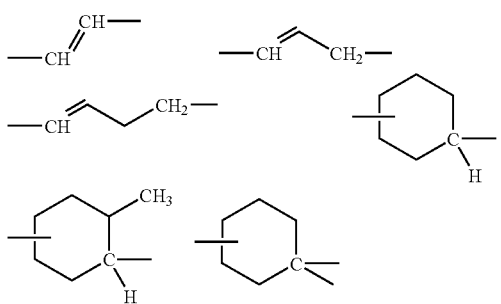

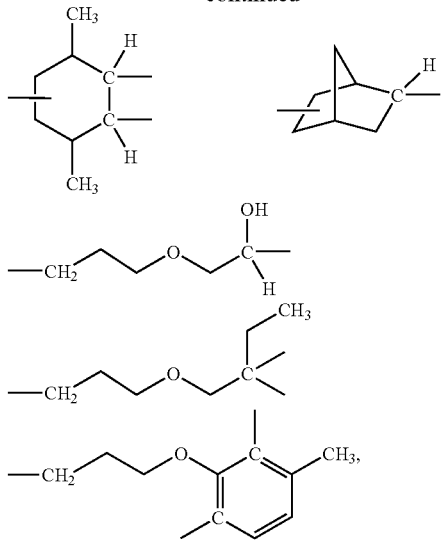

a radical of the formula

—R⁴—(Z—CH₂CH₂)$_z$—Z'—R⁴— (VII), in which the radicals R⁴ may be identical or different and is a divalent hydrocarbon radical having 1 to 10 (preferably 1 to 6) carbon atoms, Z is —O— or —NR⁵—, where R⁵ is a radical of the formula —C(O)—(CH₂)$_h$—H, where h is ≧1 (preferably 1-6, particularly preferably 1-3), Z' is the group —O—C(O)—, —NH—C(O)—, —O—C(O)O—, —NH—C(O)O— or —NH—C(O)NH—, preferably —O—C(O)—, —NH—C(O)—, —NH—C(O)O— or —NH—C(O)NH—, and z is an integer from 0 to 4 (preferably 0 or 1), and a radical of the formula (VI).

Depending on the valency of Y¹, y is preferably an integer from 2 to 10, preferably from 2 to 4.

Y² is preferably a hydrogen atom or a monovalent hydrocarbon radical having 1 to 100 carbon atom(s) which optionally may be interrupted by units —C(O)—, —C(O)O—, —C(O) NR¹—, —O—C(O)NR¹—, —NR¹—C(O)—NR¹—, —O—, —S—, =N— and substituted by hydroxyl, alkoxy, mercaptoalkyl, carbonyl, carboxyl or oxiranyl groups. It is particularly preferably a hydrogen atom or a monovalent hydrocarbon radical having 1 to 18 carbon atom(s) which optionally may be interrupted by units —C(O)—, —C(O)O—, —C(O) NR¹—, —O—C(O)NR¹—, —NR¹—C(O)—NR¹—, —O—, —S—, =N— and substituted by hydroxyl, alkoxy, mercaptoalkyl, carbonyl, carboxyl or oxiranyl groups. A hydrogen atom is particularly preferred.

Radical Y³ is preferably a hydrogen atom or a monovalent hydrocarbon radical having 1 to 100 carbon atom(s) which optionally may be interrupted by units —C(O)—, —C(O)O—, —C(O)NR¹—, —O—C(O)NR¹—, —NR¹—C(O)—NR¹—, —O—, —S—, =N— and substituted by hydroxyl, alkoxy, mercaptoalkyl, carbonyl, carboxyl or oxiranyl groups. It is particularly preferably a hydrogen atom or a monovalent hydrocarbon radical having 1 to 18 carbon atom(s) which optionally may be interrupted by units —C(O)—, —C(O)O—, —C(O)NR¹—, —O—C(O)NR¹—, —NR¹—C(O)—NR¹—, —O—, —S—, =N— and substituted by hydroxyl, alkoxy, mercaptoalkyl, carbonyl, carboxyl or oxiranyl groups. A hydrogen atom is particularly preferred.

Preferably, at least one compound selected from the aliphatic, cycloaliphatic, heterocyclic or aromatic compounds which contain at least one N-hydroxyl, oxime, nitroso, N-oxyl or N-oxy functionality is used as a mediator. Examples of such compounds are the compounds of the formulae (VIII) to (XLII) described below.

The mediators are preferably selected from the group consisting of stable nitroxyl radicals (nitroxides)—i.e. the free radicals can be obtained, characterized and stored in pure form—of the general formulae (VIII), (IX) and (X)

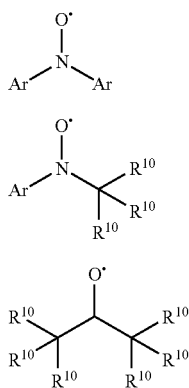

in which

Ar is a monovalent homo- or heteroaromatic mono- or dinuclear radical and in which this aromatic radical may be substituted by one or more, identical or different radicals $R^{11}$ selected from the group consisting of halogen, formyl, cyano, carbamoyl, carboxyl, ester or salt of the carboxyl radical, sulfono radical, ester or salt of the sulfono radical, sulfamoyl, nitro, nitroso, amino, phenyl, aryl-$C_1$-$C_5$-alkyl, $C_1$-$C_{12}$-alkyl, $C_1$-$C_5$-alkoxy, $C_1$-$C_{10}$-carbonyl, carbonyl-$C_1$-$C_6$-alkyl, phospho, phosphono and phosphonooxy radical, ester or salt of the phosphonooxy radical, and in which phenyl, carbamoyl and sulfamoyl radicals may be unsubstituted or monosubstituted or polysubstituted by a radical $R^{12}$, the amino radical being monosubstituted or disubstituted by $R^{12}$ and the aryl-$C_1$-$C_5$-alkyl, $C_1$-$C_{12}$-alkyl, $C_1$-$C_5$-alkoxy, $C_1$-$C_{10}$-carbonyl, carbonyl-$C_1$-$C_6$-alkyl radical may be saturated or unsaturated, branched or straight-chain and monosubstituted or polysubstituted by a radical $R^{12}$ it being possible for $R^{12}$ to be present once or several times, and $R^{12}$ are identical or different and are hydroxyl, formyl, cyano or carboxyl radical, ester or salt of the carboxyl radical, carbamoyl, sulfono, sulfamoyl, nitro, nitroso, amino, phenyl, $C_1$-$C_5$-alkyl, $C_1$-$C_5$-alkoxy or $C_1$-$C_5$-alkylcarbonyl radical, $R^{10}$ are identical or different and are a halogen, hydroxyl, mercapto, formyl, cyano, carbamoyl or carboxyl radical, ester or salt of the carboxyl radical, sulfono radical, ester or salt of the sulfono radical, sulfamoyl, nitro, nitroso, amino, phenyl, aryl-$C_1$-$C_5$-alkyl, $C_1$-$C_{12}$-alkyl, $C_1$-$C_5$-alkoxy, $C_1$-$C_{10}$-carbonyl, carbonyl-$C_1$-$C_6$-alkyl, phospho, phosphono or phosphonooxy radical, ester or salt of the phosphonooxy radical, and $R^{10}$, in the case of bicyclic stable nitroxyl radicals (structure X), may also be hydrogen, it being possible for the carbamoyl, sulfamoyl, amino, mercapto and phenyl radicals to be unsubstituted or monosubstituted or polysubstituted by a radical $R^{13}$, the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radical may be saturated or unsaturated, branched or straight-chain and may be monosubstituted or polysubstituted by a radical $R^{13}$, $R^{13}$ being identical or different and being hydroxyl, formyl, cyano or carboxyl radical, ester or salt of the carboxyl radical, carbamoyl, sulfono, sulfamoyl, nitro, nitroso, amino, phenyl, $C_1$-$C_5$-alkyl, $C_1$-$C_5$-alkoxy or $C_1$-$C_5$-alkylcarbonyl radical, and two radicals $R^{12}$ or $R^{13}$ each may be linked in pairs via a bridge $[-CR^{14}R^{15}-]_i$, where i is 0, 1, 2, 3 or 4, $R^{14}$ and $R^{15}$ being identical or different and being a halogen or carboxyl radical, ester or salt of the carboxyl radical, carbamoyl, sulfamoyl, phenyl, benzoyl, $C_1$-$C_5$-alkyl, $C_1$-$C_5$-alkoxy or $C_1$-$C_5$-alkylcarbonyl radical, and it being possible for one or more nonneighboring groups $[-CR^{14}R^{15}-]$ to be replaced by oxygen, sulfur or an optionally $C_1$-$C_5$-alkyl-substituted imino radical and for two neighboring groups $[-CR^{14}R^{15}-]$ to be replaced by a group $[-CR^{14}=CR^{15}-]$, $[-CR^{14}=N-]$ or $[-CR^{14}=N(O)-]$.

Preferred mediators are nitroxyl radicals of the general formulae (XI) and (XII)

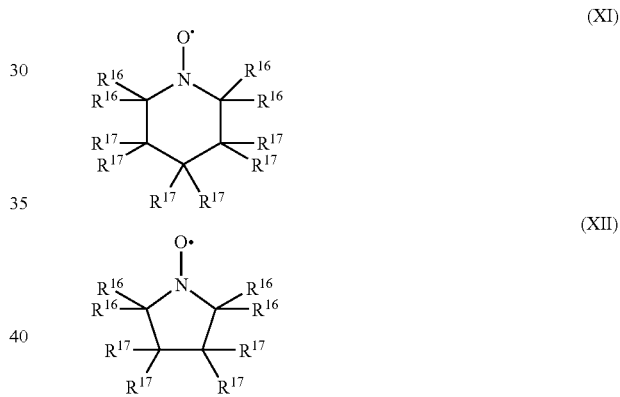

in which $R^{16}$ are identical or different and are a phenyl, aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radical, it being possible for the phenyl radicals to be unsubstituted or monosubstituted or polysubstituted by a radical $R^{18}$ and for the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radicals to be saturated or unsaturated, branched or straight-chain and to be monosubstituted or polysubstituted by a radical $R^{18}$, it being possible for $R^{18}$ to be present once or several times and $R^{18}$ being identical or different and being a hydroxyl, formyl or carboxyl radical, ester or salt of the carboxyl radical, carbamoyl, sulfono, sulfamoyl, nitro, nitroso, amino, phenyl, benzoyl, $C_1$-$C_5$-alkyl or $C_1$-$C_5$-alkoxy radical or a $C_1$-$C_5$-alkylcarbonyl radical, $R^{17}$ are identical or different and are a hydrogen atom or a hydroxyl, mercapto, formyl, cyano, carbamoyl or carboxyl radical, ester or salt of the carboxyl radical, sulfono radical, ester or salt of the sulfono radical, a sulfamoyl, nitro, nitroso, amino, phenyl, aryl-$C_1$-$C_5$-alkyl, $C_1$-$C_{12}$-alkyl, $C_1$-$C_5$- alkoxy, $C_1$-$C_{10}$-carbonyl and carbonyl-$C_1$-$C_6$-alkyl radical, phospho, phosphono or phosphonooxy radical, ester or salt of the phosphonooxy radical, it being possible for the carbamoyl, sulfamoyl, amino, mercapto and phenyl radical to be unsubstituted or monosubstituted or polysubstituted by a radical $R^{12}$, and the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radical may be saturated or unsaturated, straight-chain or branched and may be monosubstituted or polysubstituted by a radical $R^{12}$, and a [—$CR^{17}R^{17}$—] group may be replaced by oxygen, an optionally $C_1$-$C_5$-alkyl-substituted imino radical, a (hydroxy)imino radical, a carbonyl function or a vinylidene function optionally monosubstituted or disubstituted by $R^{12}$, and two neighboring groups [—$CR^{17}R^{17}$—] may be replaced by a group [—$CR^{17}$=$CR^{17}$—], [—$CR^{17}$=N—] or [—$CR^{17}$=N(O)—].

Examples of compounds of the general formulae (XI) and (XII) which may be used as mediators are
2,2,6,6-tetramethylpiperidin-1-oxyl (TEMPO),
4-hydroxy-2,2,6,6-tetramethylpiperidin-1-oxyl,
4-amino-2,2,6,6-tetramethylpiperidin-1-oxyl,
4-oxo-2,2,6,6-tetramethylpiperidin-1-oxyl,
4-acetoxy-2,2,6,6-tetramethylpiperidin-1-oxyl,
4-acetamido-2,2,6,6-tetramethylpiperidin-1-oxyl,
4-(ethoxyfluorophosphinyloxy)-2,2,6,6-tetramethylpiperidin-1-oxyl,
4-(isothiocyanato)-2,2,6,6-tetramethylpiperidin-1-oxyl,
4-maleimido-2,2,6,6-tetramethylpiperidin-1-oxyl,
4-benzoyloxy-2,2,6,6-tetramethylpiperidin-1-oxyl,
4-(4-nitrobenzoyloxy)-2,2,6,6-tetramethylpiperidin-1-oxyl,
4-(phosphonooxy)-2,2,6,6-tetramethylpiperidin-1-oxyl,
4-cyano-2,2,6,6-tetramethylpiperidin-1-oxyl,
3-carbamoyl-2,2,5,5-tetramethyl-3-pyrrolin-1-oxyl,
4-phenyl-2,2,5,5-tetramethyl-3-imidazolin-3-oxid-1-oxyl,
4-carbamoyl-2,2,5,5-tetramethyl-3-imidazolin-3-oxid-1-oxyl,
4-phenacylidene-2,2,5,5-tetramethylimidazolidin-1-oxyl,
3-(aminomethyl)-2,2,5,5-tetramethylpyrrolidin-N-oxyl,
3-carbamoyl-2,2,5,5-tetramethylpyrrolidin-N-oxyl,
3-carboxy-2,2,5,5-tetramethylpyrrolidin-N-oxyl,
3-cyano-2,2,5,5-tetramethylpyrrolidin-N-oxyl,
3-maleimido-2,2,5,5-tetramethylpyrrolidin-N-oxyl,
3-(4-nitrophenoxycarbonyl)-2,2,5,5-tetramethylpyrrolidin-N-oxyl.

In a particular embodiment, the nitroxyl radicals of the general formulae (XI) and (XII) may also be linked to a polymeric structure via one or more radicals $R^{17}$. The literature describes a large number of such polymer-bound nitroxyl radicals (cf. for example the literature cited in EP 1 302 456 A1, page 4, lines 39 to 43). Examples are PIPO (polymer immobilized piperidinyloxyl), $SiO_2$-supported TEMPO, polystyrene- and polyacrylic acid-supported TEMPO.

Preferred mediators of the general formulae (XI) and (XII) are
2,2,6,6-tetramethylpiperidin-1-oxyl (TEMPO),
4-hydroxy-2,2,6,6-tetramethylpiperidin-1-oxyl,
4-amino-2,2,6,6-tetramethylpiperidin-1-oxyl,
4-oxo-2,2,6,6-tetramethylpiperidin-1-oxyl,
4-acetoxy-2,2,6,6-tetramethylpiperidin-1-oxyl,
4-acetamido-2,2,6,6-tetramethylpiperidin-1-oxyl,
4-(isothiocyanato)-2,2,6,6-tetramethylpiperidin-1-oxyl,
4-maleimido-2,2,6,6-tetramethylpiperidin-1-oxyl,
4-benzoyloxy-2,2,6,6-tetramethylpiperidin-1-oxyl,
4-(4-nitrobenzoyloxy)-2,2,6,6-tetramethylpiperidin-1-oxyl,
4-(phosphonooxy)-2,2,6,6-tetramethylpiperidin-1-oxyl,
4-cyano-2,2,6,6-tetramethylpiperidin-1-oxyl,
3-carbamoyl-2,2,5,5-tetramethyl-3-pyrrolin-1-oxyl,
4-phenyl-2,2,5,5-tetramethyl-3-imidazolin-3-oxid-1-oxyl,
4-carbamoyl-2,2,5,5-tetramethyl-3-imidazolin-3-oxid-1-oxyl,
4-phenacylidene-2,2,5,5-tetramethylimidazolidin-1-oxyl,
PIPO (polymer immobilized piperidinyloxyl).

Particularly preferred mediators of the general formulae (XI) and (XII) are
2,2,6,6-tetramethylpiperidin-1-oxyl (TEMPO),
4-hydroxy-2,2,6,6-tetramethylpiperidin-1-oxyl,
4-amino-2,2,6,6-tetramethylpiperidin-1-oxyl,
4-acetoxy-2,2,6,6-tetramethylpiperidin-1-oxyl,
4-benzoyloxy-2,2,6,6-tetramethylpiperidin-1-oxyl and
PIPO (polymer immobilized piperidinyloxyl).

Also preferably used are mediators from the group consisting of the compounds of the general formulae (XIII), (XIV), (XV) and (XVI) of which the mediators of the general formulae (XIV), (XV) and (XVI) are preferred and the compounds of the formula (XV) and (XVI) are particularly preferred.

Compounds of the general formula (XIII) are:

in which W is one of the following groups:
[—N=N—]$_j$, [—N=$CR^{24}$—]$_j$, [—$CR^{24}$=N—]$_j$,
[—$CR^{25}$=$CR^{26}$—]$_j$,

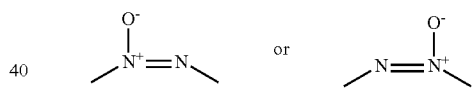

and j is 1 or 2, it being possible for the radicals $R^{21}$ to $R^{26}$ to be identical or different and, independently of one another, to be one of the following groups: hydrogen, halogen, hydroxyl, formyl, carboxyl and salts and esters thereof, amino, nitro, $C_1$-$C_{12}$-alkyl, $C_1$-$C_6$-alkoxy, carbonyl-$C_1$-$C_6$-alkyl, phenyl, sulfono, esters and salts thereof, sulfamoyl, carbamoyl, phospho, phosphono, phosphonooxy and the salts and esters thereof, it furthermore being possible for the amino, carbamoyl and sulfamoyl groups of the radicals $R^{21}$ to $R^{26}$ to be unsubstituted or monosubstituted or disubstituted by hydroxyl, $C_1$-$C_3$-alkyl or $C_1$-$C_3$-alkoxy, and it being possible for the radicals $R^{22}$ and $R^{23}$ to form a common group —B—, and —B— being one of the following groups: [—$CR^{27}$=$CR^{28}$—$CR^{29}$=$CR^{30}$—] or [—$CR^{30}$=$CR^{29}$—$CR^{28}$=$CR^{27}$—].

The radicals $R^{27}$ to $R^{30}$ may be identical or different and, independently of one another, are one of the following groups: hydrogen, halogen, hydroxyl, formyl, carboxyl and salts and esters thereof, amino, nitro, $C_1$-$C_{12}$-alkyl, $C_1$-$C_6$-alkoxy, carbonyl-$C_1$-$C_6$-alkyl, phenyl, sulfono, esters and salts thereof, sulfamoyl, carbamoyl, phospho, phosphono, phosphonooxy and salts and esters thereof, it furthermore being possible for the amino, carbamoyl and sulfamoyl groups of the radicals $R^{27}$ to $R^{30}$ to be unsubstituted or monosubstituted or disubstituted by hydroxyl, $C_1$-$C_3$-alkyl or $C_1$-$C_3$-alkoxy, and it being possible for the $C_1$-$C_{12}$-alkyl, $C_1$-$C_6$-alkoxy, carbonyl-$C_1$-$C_6$-alkyl, phenyl and aryl groups of the radicals $R^{27}$ to $R^{30}$ to be unsubstituted or furthermore monosubstituted or polysubstituted by the radical $R^{31}$, and it being possible for the radical $R^{31}$ to be one of the following groups:

hydrogen, halogen, hydroxyl, formyl, carboxyl and the salts and esters thereof, amino, nitro, $C_1$-$C_{12}$-alkyl, $C_1$-$C_6$-alkoxy, carbonyl-$C_1$-$C_6$-alkyl, phenyl, aryl and the esters and salts thereof, it being possible for the carbamoyl, sulfamoyl and amino groups of the radical $R^{31}$ to be unsubstituted or furthermore monosubstituted or disubstituted by the radical $R^{32}$ and it being possible for the radical $R^{32}$ to be one of the following groups: hydrogen, hydroxyl, formyl, carboxyl and the salts and esters thereof, amino, nitro, $C_1$-$C_{12}$-alkyl, $C_1$-$C_6$-alkoxy, carbonyl-$C_1$-$C_6$-alkyl, phenyl or aryl.

Examples of said compounds of the general formula (XIII) are:
1-hydroxy-1,2,3-triazole-4,5-dicarboxylic acid
1-phenyl-1H-1,2,3-triazole 3-oxide
5-chloro-1-phenyl-1H-1,2,3-triazole 3-oxide
5-methyl-1-phenyl-1H-1,2,3-triazole 3-oxide
4-(2,2-dimethylpropanoyl)-1-hydroxy-1H-1,2,3-triazole
4-hydroxy-2-phenyl-2H-1,2,3-triazole 1-oxide
2,4,5-triphenyl-2H-1,2,3-triazole 1-oxide
1-benzyl-1H-1,2,3-triazole 3-oxide
1-benzyl-4-chloro-1H-1,2,3-triazole 3-oxide
1-benzyl-4-bromo-1H-1,2,3-triazole 3-oxide
1-benzyl-4-methoxy-1H-1,2,3-triazole 3-oxide.

Compounds of the general formula (XIV) are

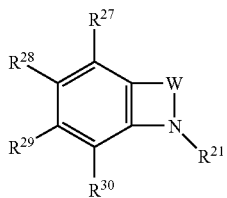

(XIV)

in which W is one of the following groups:
$[-N=N-]_j$, $[-N=CR^{24}-]_j$, $[-CR^{24}=N-]_j$, $[-CR^{25}=CR^{26}-]_j$,

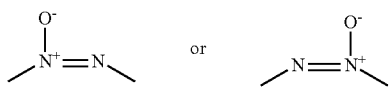

and j is 1 or 2.

The radicals $R^{21}$ and $R^{24}$ to $R^{30}$ may be identical or different and, independently of one another, are one of the following groups: hydrogen, halogen, hydroxyl, formyl, carboxyl and salts and esters thereof, amino nitro, $C_1$-$C_{12}$-alkyl, $C_1$-$C_6$-alkoxy, carbonyl-$C_1$-$C_6$-alkyl, phenyl, sulfono, esters and salts thereof, sulfamoyl, carbamoyl, phospho, phosphono, phosphonooxy and salts and esters thereof, it furthermore being possible for the amino, carbamoyl and sulfamoyl groups of the radicals $R^{21}$ and $R^{24}$ to $R^{30}$ to be unsubstituted or monosubstituted or disubstituted by hydroxyl, $C_1$-$C_3$-alkyl or $C_1$-$C_3$-alkoxy, and it being possible for the $C_1$-$C_{12}$-alkyl, $C_1$-$C_6$-alkoxy, carbonyl-$C_1$-$C_6$-alkyl, phenyl, aryl and aryl-$C_1$-$C_6$-alkyl groups of the radicals $R^{21}$ and $R^{24}$ to $R^{30}$ to be unsubstituted or furthermore monosubstituted or polysubstituted by the radical $R^{32}$ and it being possible for the radical $R^{32}$ to be one of the following groups: hydrogen, halogen, hydroxyl, formyl, carboxyl and the salts and esters thereof, amino, nitro, $C_1$-$C_{12}$-alkyl, $C_1$-$C_6$-alkoxy, carbonyl-$C_1$-$C_6$-alkyl, phenyl, aryl, sulfono, sulfeno, sulfino- and the salts and esters thereof, it being possible for the carbamoyl, sulfamoyl and amino groups of the radical $R^{32}$ to be unsubstituted or furthermore monosubstituted or disubstituted by the radical $R^{33}$ and it being possible for the radical $R^{33}$ to be one of the following groups: hydrogen, hydroxyl, formyl, carboxyl and the salts and esters thereof, amino, nitro, $C_1$-$C_{12}$-alkyl, $C_1$-$C_6$-alkoxy, carbonyl-$C_1$-$C_6$-alkyl, phenyl or aryl.

Examples of said compounds of the general formula (XIV) are:

A) 1-hydroxybenzimidazoles, such as, for example,
1-hydroxybenzimidazole-2-carboxylic acid
1-hydroxybenzimidazole
2-methyl-1-hydroxybenzimidazole
2-phenyl-1-hydroxybenzimidazole B) 1-hydroxyindoles, such as, for example,
2-phenyl-1-hydroxyindole.

Compounds of the general formula (XV) are:

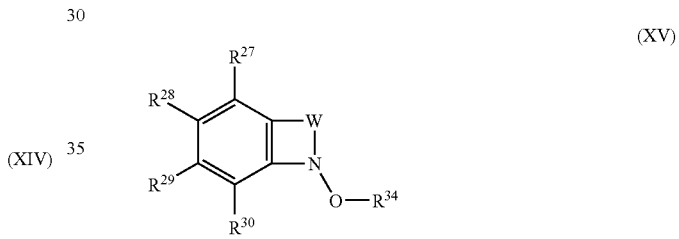

(XV)

in which W is one of the following groups:
$[-N=N-]_j$, $[-N=CR^{24}-]_j$, $[-CR^{24}=N-]_j$, $[-CR^{25}=CR^{26}-]_j$,

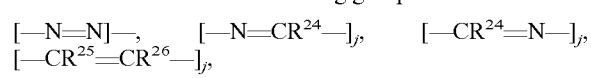

and j is 1 or 2.

The statements made above are applicable to the radicals $R^{27}$ to $R^{30}$ and $R^{24}$ to $R^{26}$.

Radical $R^{34}$ may be: hydrogen, $C_1$-$C_{10}$-alkyl, $C_1$-$C_{10}$-alkylcarbonyl and the salts and esters thereof, it being possible for the $C_1$-$C_{10}$-alkyl and $C_1$-$C_{10}$-alkylcarbonyl radicals to be unsubstituted or monosubstituted or polysubstituted by a radical $R^{35}$, it being possible for $R^{35}$ to be one of the following groups:

hydrogen, halogen, hydroxyl, formyl, carboxyl and salts and esters thereof, amino, nitro, $C_1$-$C_{12}$-alkyl, $C_1$-$C_6$-alkoxy, carbonyl-$C_1$-$C_6$-alkyl, phenyl, sulfono, the esters and salts thereof, sulfamoyl, carbamoyl, phospho, phosphono, phosphonooxy and the salts and esters thereof, it furthermore being possible for the amino, carbamoyl and sulfamoyl groups of the radical $R^{35}$ to be unsubstituted or monosubstituted or disubstituted by hydroxyl, $C_1$-$C_3$-alkyl or $C_1$-$C_3$-alkoxy.

Among the substances of the formula (XV), derivatives of 1-hydroxybenzotriazole and of the tautomeric benzotriazole 1-oxide and the esters and salts thereof are particularly preferred (compounds of the formula (XVI)):

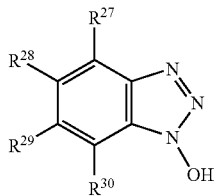
(XVI)

The radicals $R^{27}$ and $R^{30}$ may be identical or different and, independently of one another, are one of the following groups: hydrogen, halogen, hydroxyl, formyl, carboxyl and salts and esters thereof, amino, nitro, $C_1$-$C_{12}$-alkyl, $C_1$-$C_6$-alkoxy, carbonyl-$C_1$-$C_6$-alkyl, phenyl, sulfono and esters and salts thereof, sulfamoyl, carbamoyl, phospho, phosphono, phosphonooxy and salts and esters thereof, it furthermore being possible for the amino, carbamoyl and sulfamoyl groups—of the radicals $R^{27}$ to $R^{30}$ to be unsubstituted or monosubstituted or disubstituted by hydroxyl, $C_1$-$C_3$-alkyl or $C_1$-$C_3$-alkoxy, and it being possible for the $C_1$-$C_{12}$-alkyl, $C_1$-$C_6$-alkoxy, carbonyl-$C_1$-$C_6$-alkyl, phenyl and aryl groups of the radicals $R^{27}$ to $R^{30}$ to be unsubstituted or furthermore monosubstituted or polysubstituted by the radical $R^{36}$ and it being possible for the radical $R^{36}$ to be one of the following groups:

hydrogen, halogen, hydroxyl, formyl, carboxyl and the salts and esters thereof, amino, nitro, $C_1$-$C_{12}$-alkyl, $C_1$-$C_6$-alkoxy, carbonyl-$C_1$-$C_6$-alkyl, phenyl, aryl, sulfono, sulfeno, sulfino and the esters and salts thereof, it being possible for the carbamoyl, sulfamoyl and amino groups of the radical $R^{36}$ to be unsubstituted or furthermore monosubstituted or polysubstituted by the radical $R^{37}$ and it being possible for the radical $R^{37}$ to be one of the following groups:

hydrogen, hydroxyl, formyl, carboxyl and salts and esters thereof, amino, nitro, $C_1$-$C_{12}$-alkyl, $C_1$-$C_6$-alkoxy, carbonyl-$C_1$-$C_6$-alkyl, phenyl or aryl.

Examples of said compounds of the general formula (XVI) are:

A) 1H-hydroxybenzotriazoles, such as, for example,
1-hydroxybenzotriazole
1-hydroxybenzotriazole, sodium salt
1-hydroxybenzotriazole, potassium salt
1-hydroxybenzotriazole, lithium salt
1-hydroxybenzotriazole, ammonium salt
1-hydroxybenzotriazole, calcium salt
1-hydroxybenzotriazole, magnesium salt
1-hydroxybenzotriazole-6-sulfonic acid
1-hydroxybenzotriazole-6-sulfonic acid, monosodium salt
1-hydroxybenzotriazole-6-carboxylic acid
1-hydroxybenzotriazole-6-N-phenylcarboxamide
5-ethoxy-6-nitro-1-hydroxybenzotriazole
4-ethyl-7-methyl-6-nitro-1-hydroxybenzotriazole
2,3-bis(4-ethoxyphenyl)-4,6-dinitro-2,3-dihydro-1-hydroxybenzotriazole
2,3-bis(2-bromo-4-methylphenyl)-4,6-dinitro-2,3-dihydro-1-hydroxybenzotriazole
2,3-bis(4-bromophenyl)-4,6-dinitro-2,3-dihydro-1-hydroxybenzotriazole
2,3-bis(4-carboxyphenyl)-4,6-dinitro-2,3-dihydro-1-hydroxybenzotriazole
4,6-bis(trifluoromethyl)-1-hydroxybenzotriazole
5-bromo-1-hydroxybenzotriazole
6-bromo-1-hydroxybenzotriazole
4-bromo-7-methyl-1-hydroxybenzotriazole
5-bromo-7-methyl-6-nitro-1-hydroxybenzotriazole
4-bromo-6-nitro-1-hydroxybenzotriazole
6-bromo-4-nitro-1-hydroxybenzotriazole
4-chloro-1-hydroxybenzotriazole
5-chloro-1-hydroxybenzotriazole
6-chloro-1-hydroxybenzotriazole
6-chloro-5-isopropyl-1-hydroxybenzotriazole
5-chloro-6-methyl-1-hydroxybenzotriazole
6-chloro-5-methyl-1-hydroxybenzotriazole
4-chloro-7-methyl-6-nitro-1-hydroxybenzotriazole
4-chloro-5-methyl-1-hydroxybenzotriazole
5-chloro-4-methyl-1-hydroxybenzotriazole
4-chloro-6-nitro-1-hydroxybenzotriazole
6-chloro-4-nitro-1-hydroxybenzotriazole
7-chloro-1-hydroxybenzotriazole
6-diacetylamino-1-hydroxybenzotriazole
2,3-dibenzyl-4,6-dinitro-2,3-dihydro-1-hydroxybenzotriazole
4,6-dibromo-1-hydroxybenzotriazole
4,6-dichloro-1-hydroxybenzotriazole
5,6-dichloro-1-hydroxybenzotriazole
4,5-dichloro-1-hydroxybenzotriazole
4,7-dichloro-1-hydroxybenzotriazole
5,7-dichloro-6-nitro-1-hydroxybenzotriazole
5,6-dimethoxy-1-hydroxybenzotriazole
2,3-di-[2]naphthyl-4,6-dinitro-2,3-dihydro-1-hydroxybenzotriazole
4,6-dinitro-1-hydroxybenzotriazole
4,6-dinitro-2,3-diphenyl-2,3-dihydro-1-hydroxybenzotriazole
4,6-dinitro-2,3-di-p-tolyl-2,3-dihydro-1-hydroxybenzotriazole
5-hydrazino-7-methyl-4-nitro-1-hydroxybenzotriazole
5,6-dimethyl-1-hydroxybenzotriazole
4-methyl-1-hydroxybenzotriazole
5-methyl-1-hydroxybenzotriazole
6-methyl-1-hydroxybenzotriazole
5-(1-methylethyl)-1-hydroxybenzotriazole
4-methyl-6-nitro-1-hydroxybenzotriazole
6-methyl-4-nitro-1-hydroxybenzotriazole
5-methoxy-1-hydroxybenzotriazole
6-methoxy-1-hydroxybenzotriazole
7-methyl-6-nitro-1-hydroxybenzotriazole
4-nitro-1-hydroxybenzotriazole
6-nitro-1-hydroxybenzotriazole
6-nitro-4-phenyl-1-hydroxybenzotriazole
5-phenylmethyl-1-hydroxybenzotriazole
4-trifluoromethyl-1-hydroxybenzotriazole
5-trifluoromethyl-1-hydroxybenzotriazole
6-trifluoromethyl-1-hydroxybenzotriazole
4,5,6,7-tetrachloro-1-hydroxybenzotriazole
4,5,6,7-tetrafluoro-1-hydroxybenzotriazole
6-tetrafluoroethyl-1-hydroxybenzotriazole
4,5,6-trichloro-1-hydroxybenzotriazole
4,6,7-trichloro-1-hydroxybenzotriazole
6-sulfamido-1-hydroxybenzotriazole
6-N,N-diethylsulfamido-1-hydroxybenzotriazole
6-N-methylsulfamido-1-hydroxybenzotriazole
6-(1H-1,2,4-triazol-1-ylmethyl)-1-hydroxybenzotriazole 6-(5,6,7,8-tetrahydroimidazol-[1,5-a]pyridin-5-yl)-1-hydroxybenzotriazole
6-(phenyl-1H-1,2,4-triazol-1-ylmethyl)-1-hydroxybenzotriazole
6-[(5-methyl-1H-imidazol-1-yl)phenylmethyl]-1-hydroxybenzotriazole
6-[(4-methyl-1H-imidazol-1-yl)phenylmethyl]-1-hydroxybenzotriazole
6-[(2-methyl-1H-imidazol-1-yl)phenylmethyl]-1-hydroxybenzotriazole
6-(1H-imidazol-1-ylphenylmethyl)-1-hydroxybenzotriazole
5-(1H-imidazol-1-ylphenylmethyl)-1-hydroxybenzotriazole
6-[1-(1H-imidazol-1-yl)ethyl]-1-hydroxybenzotriazole monohydrochloride B) 3H-benzotriazole 1-oxides, such as, for example,
3H-benzotriazole 1-oxide
6-acetyl-3H-benzotriazole 1-oxide
5-ethoxy-6-nitro-3H-benzotriazole 1-oxide
4-ethyl-7-methyl-6-nitro-3H-benzotriazole 1-oxide
6-amino-3,5-dimethyl-3H-benzotriazole 1-oxide
6-amino-3-methyl-3H-benzotriazole 1-oxide
5-bromo-3H-benzotriazole 1-oxide
6-bromo-3H-benzotriazole 1-oxide
4-bromo-7-methyl-3H-benzotriazole 1-oxide
5-bromo-4-chloro-6-nitro-3H-benzotriazole 1-oxide
4-bromo-6-nitro-3H-benzotriazole 1-oxide
6-bromo-4-nitro-3H-benzotriazole 1-oxide
5-chloro-3H-benzotriazole 1-oxide
6-chloro-3H-benzotriazole 1-oxide
4-chloro-6-nitro-3H-benzotriazole 1-oxide
4,6-dibromo-3H-benzotriazole 1-oxide
4,6-dibromo-3-methyl-3H-benzotriazole 1-oxide
4,6-dichloro-3H-benzotriazole 1-oxide
4,7-dichloro-3H-benzotriazole 1-oxide
5,6-dichloro-3H-benzotriazole 1-oxide
4,6-dichloro-3-methyl-3H-benzotriazole 1-oxide
5,7-dichloro-6-nitro-3H-benzotriazole 1-oxide
3,6-dimethyl-6-nitro-3H-benzotriazole 1-oxide
3,5-dimethyl-6-nitro-3H-benzotriazole 1-oxide
3-methyl-3H-benzotriazole 1-oxide
5-methyl-3H-benzotriazole 1-oxide
6-methyl-3H-benzotriazole 1-oxide
6-methyl-4-nitro-3H-benzotriazole 1-oxide
7-methyl-6-nitro-3H-benzotriazole 1-oxide
5-chloro-6-nitro-3H-benzotriazole 1-oxide C) 2H-benzotriazole 1-oxides, such as, for example,
2-(4-acetoxyphenyl)-2H-benzotriazole 1-oxide
6-acetylamino-2-phenyl-2H-benzotriazole 1-oxide
2-(4-ethylphenyl)-4,6-dinitro-2H-benzotriazole 1-oxide
2-(3-aminophenyl)-2H-benzotriazole 1-oxide
2-(4-aminophenyl)-2H-benzotriazole 1-oxide
6-amino-2-phenyl-2H-benzotriazole 1-oxide
5-bromo-4-chloro-6-nitro-2-phenyl-2H-benzotriazole 1-oxide
2-(4-bromophenyl)-2H-benzotriazole 1-oxide
5-bromo-2-phenyl-2H-benzotriazole 1-oxide
6-bromo-2-phenyl-2H-benzotriazole 1-oxide
2-(4-bromophenyl)-4,6-dinitro-2H-benzotriazole 1-oxide
2-(4-bromophenyl)-6-nitro-2H-benzotriazole 1-oxide
5-chloro-2-(2-chlorophenyl)-2H-benzotriazole 1-oxide
5-chloro-2-(3-chlorophenyl)-2H-benzotriazole 1-oxide
5-chloro-2-(2-chlorophenyl)-2H-benzotriazole 1-oxide
5-chloro-2-(3-chlorophenyl)-2H-benzotriazole 1-oxide
5-chloro-2-(2,4-dibromophenyl)-2H-benzotriazole 1-oxide
5-chloro-2-(2,5-dimethylphenyl)-2H-benzotriazole 1-oxide
5-chloro-2-(4-nitrophenyl)-2H-benzotriazole 1-oxide
5-chloro-6-nitro-2-phenyl-2H-benzotriazole 1-oxide
2-[4-(4-chloro-3-nitrophenylazo)-3-nitrophenyl]-4,6-dinitro-2H-benzotriazole 1-oxide
2-(3-chloro-4-nitrophenyl)-4,6-dinitro-2H-benzotriazole 1-oxide
2-(4-chloro-3-nitrophenyl)-4,6-dinitro-2H-benzotriazole 1-oxide
4-chloro-6-nitro-2-p-tolyl-2H-benzotriazole 1-oxide
5-chloro-6-nitro-2-p-tolyl-2H-benzotriazole 1-oxide
6-chloro-4-nitro-2-p-tolyl-2H-benzotriazole 1-oxide
2-(2-chlorophenyl)-2H-benzotriazole 1-oxide
2-(3-chlorophenyl)-2H-benzotriazole 1-oxide
2-(4-chlorophenyl)-2H-benzotriazole 1-oxide
5-chloro-2-phenyl-2H-benzotriazole 1-oxide
2-[4-(4-chlorophenylazo)-3-nitrophenyl]-4,6-dinitro-2H-benzotriazole 1-oxide
2-(2-chlorophenyl)-4,6-dinitro-2H-benzotriazole 1-oxide
2-(3-chlorophenyl)-4,6-dinitro-2H-benzotriazole-1-oxide
2-(4-chlorophenyl)-4,6-dinitro-2H-benzotriazole 1-oxide
2-{4-[N'-(3-chlorophenyl)hydrazino]-3-nitrophenyl}-4,6-dinitro-2H-benzotriazole 1-oxide
2-{4-[N'-(4-chlorophenyl)hydrazino]-3-nitrophenyl}-4,6-dinitro-2H-benzotriazole 1-oxide
2-(2-chlorophenyl)-6-methyl-2H-benzotriazole 1-oxide
2-(3-chlorophenyl)-6-methyl-2H-benzotriazole 1-oxide
2-(4-chlorophenyl)-6-methyl-2H-benzotriazole 1-oxide
2-(3-chlorophenyl)-6-nitro-2H-benzotriazole 1-oxide
2-(4-chlorophenyl)-6-nitro-2H-benzotriazole 1-oxide
2-(4-chlorophenyl)-6-picrylazo-2H-benzotriazole 1-oxide
5-chloro-2-(2,4,5-trimethylphenyl)-2H-benzotriazole 1-oxide
4,5-dibromo-6-nitro-2-p-tolyl-2H-benzotriazole 1-oxide
4,5-dichloro-6-nitro-2-phenyl-2H-benzotriazole 1-oxide
4,5-dichloro-6-nitro-2-p-tolyl-2H-benzotriazole 1-oxide
4,7-dichloro-6-nitro-2-p-tolyl-2H-benzotriazole 1-oxide
4,7-dimethyl-6-nitro-2-phenyl-2H-benzotriazole 1-oxide
2-(2,4-dimethylphenyl)-4,6-dinitrobenzotriazole 1-oxide
2-(2,5-dimethylphenyl)-4,6-dinitro-2H-benzotriazole 1-oxide
2-(2,4-dimethylphenyl)-6-nitro-2H-benzotriazole 1-oxide
2-(2,5-dimethylphenyl)-6-nitro-2H-benzotriazole 1-oxide
4,6-dinitro-2-[3-nitro-4-(N-phenylhydrazino)phenyl)-2H-benzotriazole 1-oxide
4,6-dinitro-2-[4-nitro-4-(N'-phenylhydrazino)phenyl]-2H-benzotriazole 1-oxide
4,6-dinitro-2-phenyl-2H-benzotriazole 1-oxide
2-(2,4-dinitrophenyl)-4,6-dinitro-2H-benzotriazole 1-oxide
2-(2,4-dinitrophenyl)-6-nitro-2H-benzotriazole 1-oxide
4,6-dinitro-2-o-tolyl-2H-benzotriazole 1-oxide
4,6-dinitro-2-p-tolyl-2H-benzotriazole 1-oxide
4,6-dinitro-2-(2,4,5-trimethylphenyl)-2H-benzotriazole 1-oxide
2-(4-methoxyphenyl)-2H-benzotriazole 1-oxide
2-(4-methoxyphenyl)-6-methyl-2H-benzotriazole 1-oxide
5-methyl-6-nitro-2-m-tolyl-2H-benzotriazole 1-oxide
5-methyl-6-nitro-2-o-tolyl-2H-benzotriazole 1-oxide
5-methyl-6-nitro-2-p-tolyl-2H-benzotriazole 1-oxide
6-methyl-4-nitro-2-p-tolyl-2H-benzotriazole 1-oxide
6-methyl-2-phenyl-2H-benzotriazole 1-oxide
4-methyl-2-m-tolyl-2H-benzotriazole 1-oxide
4-methyl-2-o-tolyl-2H-benzotriazole 1-oxide
4-methyl-2-p-tolyl-2H-benzotriazole 1-oxide
6-methyl-2-m-tolyl-2H-benzotriazole 1-oxide
6-methyl-2-o-tolyl-2H-benzotriazole 1-oxide
6-methyl-2-p-tolyl-2H-benzotriazole 1-oxide
2-[1]naphthyl-4-6-dinitro-2H-benzotriazole 1-oxide
2-[2]naphthyl-4-6-dinitro-2H-benzotriazole 1-oxide 2-[1]naphthyl-6-nitro-2H-benzotriazole 1-oxide
2-[2]naphthyl-6-nitro-2H-benzotriazole 1-oxide
2-(3-nitrophenyl)-2H-benzotriazole 1-oxide
6-nitro-2-phenyl-2H-benzotriazole 1-oxide
4-nitro-2-p-tolyl-2H-benzotriazole 1-oxide
6-nitro-2-o-tolyl-2H-benzotriazole 1-oxide
6-nitro-2-p-tolyl-2H-benzotriazole 1-oxide
6-nitro-2-(2,4,5-trimethylphenyl)-2H-benzotriazole 1-oxide
2-phenyl-2H-benzotriazole 1-oxide
2-o-tolyl-2H-benzotriazole 1-oxide
2-p-tolyl-2H-benzotriazole 1-oxide.

Preferably used as mediators are furthermore those from the group consisting of cyclic N-hydroxy compounds having at least one optionally substituted five- or six-membered ring, containing the structural unit of the formula (XVII)

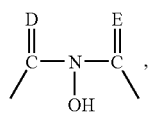

(XVII)

and the salts, ethers or esters thereof, in which D and E are identical or different and are O, S, or $NR^{38}$, where $R^{38}$ is hydrogen, hydroxyl, formyl, carbamoyl or sulfono radical, ester or salt of the sulfono radical, sulfamoyl, nitro, amino, phenyl, aryl-$C_1$-$C_5$-alkyl, $C_1$-$C_{12}$-alkyl, $C_1$-$C_5$-alkoxy, $C_1$-$C_{10}$-carbonyl, carbonyl-$C_1$-$C_6$-alkyl, phospho, phosphono or phosphonooxy radical, ester or salt of the phosphonooxy radical, it being possible for carbamoyl, sulfamoyl, amino and phenyl radicals to be unsubstituted or monosubstituted or polysubstituted by a radical $R^{39}$ and it being possible for the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radicals to be saturated or unsaturated, branched or straight-chain, and to be monosubstituted or polysubstituted by a radical $R^{39}$, $R^{39}$ being identical or different and being a hydroxyl, formyl or carboxyl radical, ester or salt of the carboxyl radical, carbamoyl or sulfono radical, ester or salt of the sulfono radical, sulfamoyl, nitro, amino, phenyl, $C_1$-$C_5$-alkyl or $C_1$-$C_5$-alkoxy radical.

Preferred mediators from the group consisting of cyclic N-hydroxy compounds are the compounds of the general formulae (XVIII), (XIX), (XX) and (XXI), in which compounds of the general formulae (XVIII), (XIX), (XX) and (XXI), in which D and E have the meaning of O or S are particularly preferred:

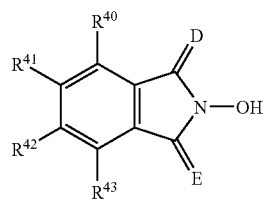

(XVIII)

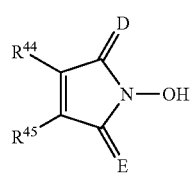

(XIX)

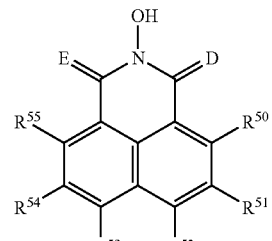

(XX)

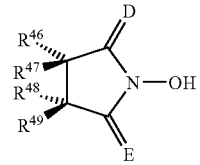

(XXI)

in which D and E have the abovementioned meaning, the radicals $R^{40}$ to $R^{55}$ are identical or different and are halogen radical, carboxyl radical, salt or ester of a carboxyl radical or the meanings stated for $R^{38}$, it not being permitted for $R^{46}$ and $R^{47}$ or $R^{48}$ and $R^{49}$ simultaneously to be a hydroxyl or amino radical and it optionally being possible for two substituents $R^{40}$-$R^{43}$, $R^{44}$-$R^{45}$, $R^{46}$-$R^{49}$, $R^{50}$-$R^{55}$ each to be linked to form a ring —F—, —F— having one of the following meanings:

[—CH=CH—]$_k$ where k=1 to 3,

—CH=CH—CH=N— or

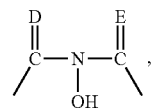

(XVII)

and it optionally being possible for the radicals $R^{46}$-$R^{49}$ also to be linked to one another by one or two bridge elements -G-, where -G- are identical or different and have the meaning of —O—, —S—, —CH$_2$— and —CR$^{56}$=CR$^{57}$—, where $R^{56}$ and $R^{57}$ are identical or different and have the meaning of $R^{40}$.

Examples of compounds of the general formulae (XVIII), (XIX), (XX) and (XXI) are N-hydroxyphthalimide and optionally substituted N-hydroxyphthalimide derivatives, N-hydroxymaleimide and optionally substituted N-hydroxymaleimide derivatives, N-hydroxy-naphthalimide and optionally substituted N-hydroxy-naphthalimide derivatives, N-hydroxysuccinimide and optionally substituted N-hydroxysuccinimide derivatives, preferably those in which the radicals $R^{46}$-$R^{49}$ are linked in polycyclic form.

Examples of compounds of the formula (XVIII) which are suitable as mediator are:
N-hydroxyphthalimide,
3-amino-N-hydroxyphthalimide,
4-amino-N-hydroxyphthalimide,
N-hydroxybenzene-1,2,4-tricarboximide,
N,N'-dihydroxypyromellitic acid diimide,
N,N'-dihydroxybenzophenone-3,3', 4,4'-tetracarboxylic acid diimide.

Examples of compounds of the formula (XIX) which are suitable as a mediator are:

N-hydroxymaleimide,
pyridine-2,3-dicarboxylic acid N-hydroxyimide.

An example of a compound of the formula (XX) which is suitable as a mediator is:
N-hydroxynaphthalimide sodium salt.

An example of a compound which is suitable as a mediator and has a six-membered ring containing the structural unit of the formula (XVII) is:
N-hydroxyglutarimide.

Examples of compounds of the formula (XXI) which are suitable as a mediator are:
N-hydroxysuccinimide,
N-hydroxytartarimide,
N-hydroxy-5-norbornene-2,3-dicarboximide,
exo-N-hydroxy-7-oxabicyclo[2.2.1]hept-5-ene-2,3-dicarboximide,
N-hydroxy-cis-cyclohexane-1,2-dicarboximide,
N-hydroxy-cis-4-cyclohexene-1,2-dicarboximide.

All compounds mentioned by way of example are of course also suitable as mediators in the form of their salts or esters.

Furthermore, the mediators can preferably be selected from the group consisting of the N-aryl-N-hydroxyamides. Among these, preferably used mediators are the compounds of the general formulae (XXII), (XXIII) or (XXIV)

$$\text{I—N(OH)—J} \qquad \text{(XXII)}$$

$$\text{I—N(OH)—K—N(OH)—I} \qquad \text{(XXIII)}$$

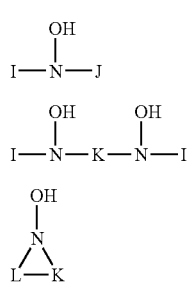
(XXIV)

and the salts, ethers or esters thereof, in which

I is a monovalent, homo- or heteroaromatic, mono- or dinuclear radical, and

J is a monovalent acid radical, present in amide form, of acids selected from the group consisting of carboxylic acid having up to 20 carbon atoms, carbonic acid, monoesters of carbonic acid or of carbamic acid, sulfonic acid, phosphonic acid, phosphoric acid, monoesters or diesters of phosphoric acid, and K is a divalent acid radical, present in amide form, of acids selected from the group consisting of mono- and dicarboxylic acids having up to 20 carbon atoms, carbonic acid, sulfonic acid, phosphonic acid, phosphoric acid and monoesters of phosphoric acid, and L is a divalent, homo- or heteroaromatic, mono- or dinuclear radical, it being possible for these aromatics to be substituted by one or more, identical or different radicals $R^{58}$, where $R^{58}$ is selected from the group consisting of halogen, hydroxyl, formyl, cyano, carbamoyl and carboxyl radical, ester or salt of the carboxyl radical, sulfono radical, sulfamoyl, nitro, nitroso, amino, phenyl, aryl-$C_1$-$C_5$-alkyl, $C_1$-$C_{12}$-alkyl, $C_1$-$C_5$-alkoxy, $C_1$-$C_{10}$-carbonyl, carbonyl-$C_1$-$C_6$-alkyl, phospho, phosphono and phosphonooxy radical, ester or salt of the phosphonooxy radical, it being possible for the carbamoyl, sulfamoyl, amino and phenyl radicals to be unsubstituted or monosubstituted or polysubstituted by a radical $R^{59}$, where $R^{59}$ are identical or different and have the meaning of a hydroxyl, formyl, cyano or carboxyl radical, ester or salt of the carboxyl radical, carbamoyl, sulfono, sulfamoyl, nitro, nitroso, amino, phenyl, $C_1$-$C_5$-alkyl, $C_1$-$C_5$-alkoxy or $C_1$-$C_5$-alkylcarbonyl radical, and it being possible for the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radicals to be saturated or unsaturated, branched or straight-chain and to be monosubstituted or polysubstituted by a radical $R^{59}$, it being possible for two radicals $R^{58}$ or $R^{59}$ each to be linked in pairs by a bridge [—$CR^{60}R^{61}$—]$_i$, where i is 0, 1, 2, 3 or 4, and $R^{60}$ and $R^{61}$ are identical or different and are a carboxyl radical, ester or salt of the carboxyl radical, phenyl, $C_1$-$C_5$-alkyl, $C_1$-$C_5$-alkoxy or $C_1$-$C_5$-alkylcarbonyl radical, and one or more nonneighboring groups —$CR^{60}R^{61}$— may be replaced by oxygen, sulfur or an imino radical optionally substituted by a $C_1$ to $C_5$ alkyl radical, or two neighboring groups —$CR^{60}R^{61}$— may be replaced by a group —$CR^{60}$=$CR^{61}$—.

Particularly preferred mediators from the group consisting of N-aryl-N-hydroxyamides are the compounds of the general formulae (XXV), (XXVI), (XXVII), (XXVIII) or (XXIX):

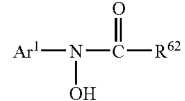
(XXV)

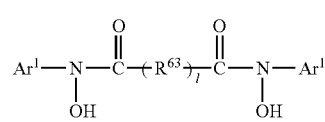
(XXVI)

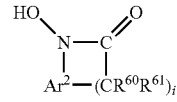
(XXVII)

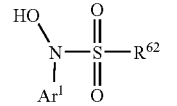
(XXVIII)

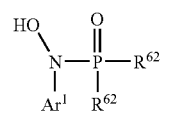
(XXIX)

and the salts, ethers or esters thereof, in which $Ar^1$ is a monovalent, homo- or heteroaromatic, mononuclear aryl radical, and $Ar^2$ is a divalent, homo- or heteroaromatic, mononuclear aryl radical, which may be substituted by one or more, identical or different radicals $R^{64}$, where $R^{64}$ is selected from the group consisting of a hydroxyl, cyano and carboxyl radical, ester or salt of the carboxyl radical, sulfono radical, ester or salt of the sulfono radical, nitro, nitroso, amino, $C_1$-$C_{12}$-alkyl, $C_1$-$C_5$-alkoxy, $C_1$-$C_{10}$-carbonyl and carbonyl-$C_1$-$C_6$-alkyl radical, it being possible for the amino radicals to be unsubstituted or monosubstituted or polysubstituted by a radical $R^{65}$, where $R^{65}$ are identical or different and are selected from the group consisting of hydroxyl and carboxyl radical, ester or salt of the carboxyl radical, sulfono, nitro, amino, $C_1$-$C_5$-alkyl, $C_1$-$C_5$-alkoxy and $C_1$-$C_5$-alkylcarbonyl radical, and it being possible for the $C_1$-$C_{12}$-alkyl, $C_1$-$C_5$-alkoxy, $C_1$-$C_{10}$-carbonyl and carbonyl-$C_1$-$C_6$-alkyl radical to be saturated or unsaturated, branched or straight-chain and monosubstituted or polysubstituted by a radical $R^{65}$, two radicals $R^{64}$ each in pairs may be linked via a bridge [—$CR^{60}R^{61}$—]$_i$, $R^{60}$, $R^{61}$ and i having the abovementioned meanings, it being possible for one or more nonneighboring groups —$CR^{60}R^{61}$— to be replaced by oxygen, sulfur or an imino radical which is optionally substituted by a $C_1$ to $C_5$ alkyl radical, it being possible for two neighboring groups —$CR6CR^{61}$— to be replaced by a group —$CR^{60}$═$CR^{61}$—, $R^{62}$ are identical or different monovalent radicals selected from the group consisting of hydrogen and a phenyl, aryl-$C_1$-$C_5$-alkyl, $C_1$-$C_{12}$-alkyl, $C_1$-$C_5$-alkoxy and $C_1$-$C_{10}$-carbonyl radical, it being possible for phenyl radicals to be unsubstituted or monosubstituted or polysubstituted by a radical $R^{66}$, where $R^{66}$ are identical or different and are selected from the group consisting of a hydroxyl, formyl, cyano and carboxyl radical, ester or salt of the carboxyl radical, carbamoyl, sulfono, sulfamoyl, nitro, nitroso, amino, phenyl, $C_1$-$C_5$-alkyl and $C_1$-$C_5$-alkoxy radical, and it being possible for the aryl-$C_1$-$C_5$-alkyl, $C_1$-$C_{12}$-alkyl, $C_1$-$C_5$-alkoxy and $C_1$-$C_{10}$-carbonyl radicals to be saturated or unsaturated, branched or straight-chain and monosubstituted or polysubstituted by a radical $R^{66}$, $R^{63}$ are divalent radicals selected from the group consisting of an ortho-, meta- and para-phenylene, aryl-$C_1$-$C_5$-alkylene, $C_1$-$C_{12}$-alkylene and $C_1$-$C_5$-alkylenedioxy radical, it being possible for phenylene radicals to be unsubstituted or monosubstituted or polysubstituted by a radical $R^{66}$, and it being possible for the aryl-$C_1$-$C_5$-alkylene, $C_1$-$C_{12}$-alkylene and $C_1$-$C_5$-alkylenedioxy radicals to be saturated or unsaturated, branched or straight-chain and to be monosubstituted or polysubstituted by a radical $R^{66}$, l being 0 or 1 and i having the meaning already mentioned above.

$Ar^1$ is preferably a phenyl radical and $Ar^2$ is preferably an ortho-phenylene radical, it being possible for $Ar^1$ to be substituted by up to five and $Ar^2$ by up to four, identical or different radicals selected from the group consisting of a $C_1$-$C_3$-alkyl, $C_1$-$C_3$-alkylcarbonyl and carboxyl radical, ester or salt of the carboxyl radical, sulfono radical, ester or salt of the sulfono radical, hydroxyl, cyano, nitro, nitroso and amino radical, it being possible for amino radicals to be substituted by two different radicals selected from the group consisting of hydroxyl and $C_1$-$C_3$-alkylcarbonyl.

$R^{62}$ is preferably a monovalent radical selected from the group consisting of a hydrogen, phenyl, $C_1$-$C_{12}$-alkyl and $C_1$-$C_5$-alkoxy radical, it being possible for the $C_1$-$C_{12}$-alkyl radicals and $C_1$-$C_5$-alkoxy radicals to be saturated or unsaturated, branched or straight-chain.

$R^{63}$ is preferably a divalent radical selected from the group consisting of an ortho- or para-phenylene, $C_1$-$C_{12}$-alkylene and $C_1$-$C_5$-alkylenedioxy radical, it being possible for the aryl-$C_1$-$C_5$-alkyl, $C_1$-$C_{12}$-alkyl and $C_1$-$C_5$-alkoxy radicals to be saturated or unsaturated, branched or straight-chain and to be monosubstituted or polysubstituted by a radical $R^{66}$.

$R^{66}$ is preferably a carboxyl radical, ester or salt of the carboxyl radical, carbamoyl, phenyl or $C_1$-$C_3$-alkoxy radical.

Examples of compounds of the general formulae (XXV), (XXVI), (XXVII), (XXVIII) or (XXIX) which can be used as mediators are:
N-hydroxyacetanilide,
N-hydroxypivaloylanilide,
N-hydroxyacrylanilide,
N-hydroxybenzoylanilide,
N-hydroxymethylsulfonylanilide,
N-hydroxy-N-phenylmethylcarbamate,
N-hydroxy-3-oxobutyrylanilide,
N-hydroxy-4-cyanoacetanilide,
N-hydroxy-4-methoxyacetanilide,
N-hydroxyphenacetin,
N-hydroxy-2,3-dimethylacetanilide,
N-hydroxy-2-methylacetanilide,
N-hydroxy-4-methylacetanilide,
1-hydroxy-3,4-dihydroquinolin-(1H)-2-one,
N,N'-dihydroxy-N,N'-diacetyl-1,3-phenylenediamine,
N,N'-dihydroxysuccinic acid dianilide,
N,N'-dihydroxymaleic acid dianilide,
N,N'-dihydroxyoxalic acid dianilide,
N,N'-dihydroxyphosphoric acid dianilide,
N-acetoxyacetanilide,
N-hydroxymethyloxalylanilide,
N-hydroxymaleic acid monoanilide, the following mediators being preferred:
N-hydroxyacetanilide,
N-hydroxyformanilide,
N-hydroxy-N-phenylmethylcarbamate,
N-hydroxy-2-methylacetanilide,
N-hydroxy-4-methylacetanilide,
1-hydroxy-3,4-dihydroquinolin-(1H)-2-one and
N-acetoxyacetanilide.

Furthermore, preferably used mediators are compounds from the group consisting of the N-alkyl-N-hydroxyamides, compounds of the general formulae (XXX) or (XXXI) and the salts, ethers or esters thereof being preferably used:

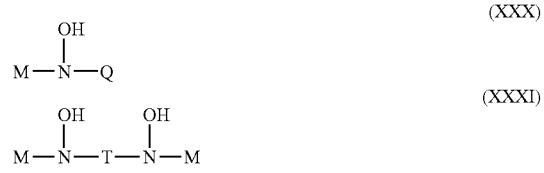

in which

M are identical or different and are a monovalent linear or branched or cyclic or polycyclic saturated or unsaturated alkyl radical having 1-24 carbon atoms, it being possible for this alkyl radical to be substituted by one or more radicals $R^{67}$, where $R^{67}$ are identical or different and are selected from the group consisting of a hydroxyl, mercapto, cyano, formyl and carboxyl radical, ester or salt of the carboxyl radical, carbamoyl, sulfamoyl and sulfono radical, ester or salt of the sulfono radical, nitro, nitroso, amino, hydroxylamino, phenyl, benzoyl, $C_1$-$C_5$-alkyl, $C_1$-$C_5$-alkoxy, $C_1$-$C_{10}$-carbonyl, phospho, phosphono and phosphonooxy radical, ester or salt of the phosphonooxy radical, it being possible for the carbamoyl, sulfamoyl, amino, hydroxylamino, mercapto and phenyl radicals to be unsubstituted or monosubstituted or polysubstituted by a radical $R^{67}$, and it being possible for the $C_1$-$C_5$-alkoxy and $C_1$-$C_{10}$-carbonyl radicals to be saturated or unsaturated, branched or straight-chain and monosubstituted or polysubstituted by a radical $R^{67}$, and it being possible for non-α-methylene groups to be replaced by oxygen, sulfur or an optionally monosubstituted imino radical, Q is a monovalent acid radical present in amidic form and of acids selected from the group consisting of aliphatic or mononuclear or dinuclear aromatic or mononuclear or dinuclear heteroaromatic carboxylic acids having up to 20 carbon atoms, carbonic acid, monoesters of carbonic acid or of carbamic acid, sulfonic acid, phosphonic acid, phosphoric acid, monoesters or diesters of phosphoric acid, T is a divalent acid radical present in amidic form and of acids selected from the group consisting of aliphatic mononuclear or dinuclear aromatic or mononuclear or dinuclear heteroaromatic dicarboxylic acids having up to 20 carbon atoms, carbonic acid, sulfonic acid, phosphonic acid, phosphoric acid, monoesters of phosphoric acid, it being possible for the alkyl radicals of the aliphatic acids Q and T present in amidic form to be linear or branched and/or cyclic and/or polycyclic, saturated or unsaturated, to contain 0-24 carbon atoms and to be unsubstituted or monosubstituted or polysubstituted by the radical $R^{68}$ where $R^{68}$ are identical or different and are selected from the group consisting of hydroxyl, mercapto, cyano, formyl, carbamoyl and carboxyl radical, ester or salt of the carboxyl radical, sulfamoyl and sulfono radical, ester or salt of the sulfono radical, nitro, nitroso, amino, phenyl, aryl-$C_1$-$C_5$-alkyl, $C_1$-$C_{12}$-alkyl, $C_1$-$C_5$-alkoxy, $C_1$-$C_{10}$-carbonyl, phospho, phosphono and phosphonooxy radical, ester or salt of the phosphonooxy radical, it being possible for the carbamoyl, sulfamoyl, amino, mercapto and phenyl radicals to be unsubstituted or monosubstituted or polysubstituted by a radical $R^{67}$ and it being possible for the aryl-$C_1$-$C_5$-alkyl, $C_1$-$C_{12}$-alkyl, $C_1$-$C_5$-alkoxy and $C_1$-$C_{10}$-carbonyl radicals to be saturated or unsaturated, branched or straight-chain and monosubstituted or polysubstituted by a radical $R^{67}$, and it being possible for the aryl and heteroaryl radicals of the aromatic or heteroaromatic acids Q and T present in amidic form to be substituted by one or more radicals $R^{68}$ which are identical or different.

Particularly preferred mediators from the group consisting of the N-alkyl-N-hydroxyamides are compounds of the general formulae (XXXII), (XXXIII), (XXXIV) or (XXXV)

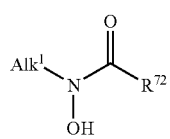

(XXXII)

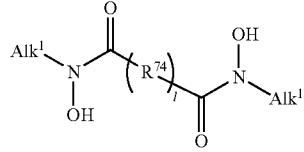

(XXXIII)

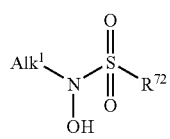

(XXXIV)

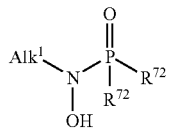

(XXXV)

and the salts, ethers or esters thereof, in which $Alk^1$ are identical or different and are a monovalent linear or branched or cyclic or polycyclic saturated or unsaturated alkyl radical having 1-10 carbon atoms, it being possible for this alkyl radical to be substituted by one or more radicals $R^{70}$ which are identical or different and are selected from the group consisting of a hydroxyl, formyl, carbamoyl and carboxyl radical, ester or salt of the carboxyl radical, sulfono radical, ester or salt of the sulfono radical, sulfamoyl, nitro, nitroso, amino, hydroxylamino, phenyl, $C_1$-$C_5$-alkoxy and $C_1$-$C_{10}$-carbonyl radicals, it being possible for the carbamoyl, sulfamoyl, amino, hydroxylamino and phenyl radicals to be unsubstituted or monosubstituted or polysubstituted by a radical $R^{71}$, where $R^{71}$ are identical or different and are selected from the group consisting of a hydroxyl, formyl, cyano and carboxyl radical, ester or salt of the carboxyl radical, carbamoyl, sulfono, sulfamoyl, nitro, amino, phenyl, benzoyl, $C_1$-$C_5$-alkyl, $C_1$-$C_5$-alkoxy and $C_1$-$C_5$-alkylcarbonyl radical, and it being possible for the $C_1$-$C_5$-alkoxy and $C_1$-$C_{10}$-carbonyl radicals to be saturated or unsaturated, branched or straight-chain and monosubstituted or polysubstituted by a radical $R^{71}$, and it being possible for non-α-methylene groups to be replaced by oxygen, sulfur or an optionally monosubstituted imino radical, $R^{72}$ are identical or different monovalent radicals selected from the group consisting of a hydrogen, phenyl, pyridyl, furyl, pyrrolyl, thienyl, aryl-$C_1$-$C_5$-alkyl, $C_1$-$C_{12}$-alkyl, $C_1$-$C_{10}$-alkoxy and $C_1$-$C_{10}$-carbonyl radical, it being possible for the phenyl, pyridyl, furyl, pyrrolyl and thienyl radicals to be unsubstituted or monosubstituted or polysubstituted by a radical $R^{27}$ and for the aryl-$C_1$-$C_5$-alkyl, $C_1$-$C_{12}$-alkyl, $C_1$-$C_{10}$-alkoxy and $C_1$-$C_{10}$-carbonyl radicals to be saturated or unsaturated, branched or straight-chain and monosubstituted or polysubstituted by a radical $R^{73}$, where $R^{73}$ are identical or different and are selected from the group consisting of a hydroxyl, formyl and carboxyl radical, ester or salt of the carboxyl radical, carbamoyl, sulfono, sulfamoyl, nitro, amino, phenyl, $C_1$-$C_5$-alkyl and $C_1$-$C_5$-alkoxy radical, $R^{74}$ are divalent radicals selected from the group consisting of phenylene, pyridylene, thienylene, furylene, pyrrolylene, aryl-$C_1$-$C_5$-alkylene, $C_1$-$C_{12}$-alkylene, $C_1$-$C_5$-alkylenedioxy radical, it being possible for the phenylene, pyridylene, thienylene, furylene and pyrrolylene to be unsubstituted or monosubstituted or polysubstituted by a radical $R^{73}$ and for the aryl-$C_1$-$C_5$-alkylene, $C_1$-$C_{12}$-alkylene and $C_1$-$C_5$-alkylenedioxy radicals to be saturated or unsaturated, branched or straight-chain and to be monosubstituted or polysubstituted by a radical $R^{73}$, and l is 0 or 1.

Preferred mediators from the group consisting of the N-alkyl-N-hydroxyamides are in particular those compounds of the general formulae (XXXII) to (XXXV) in which $Alk^1$ are identical or different and are a monovalent linear or branched or cyclic saturated or unsaturated alkyl radical having 1-10 carbon atoms, it being possible for this alkyl radical to be substituted by one or more radicals $R^{70}$ which are identical or different and are selected from the group consisting of a hydroxyl, carbamoyl and carboxyl radical, ester or salt of the carboxyl radical, sulfono radical, ester or salt of the sulfono radical, sulfamoyl, amino, phenyl, $C_1$-$C_5$-alkoxy and $C_1$-$C_5$-carbonyl radical, it being possible for the carbamoyl, sulfamoyl, amino and phenyl radicals to be unsubstituted or monosubstituted or polysubstituted by a radical $R^{71}$, where $R^{71}$ are identical or different and are selected from the group consisting of a hydroxyl and carboxyl radical, ester or salt of the carboxyl radical, carbamoyl, sulfono, sulfamoyl, nitro, amino, phenyl, benzoyl, $C_1$-$C_5$-alkyl, $C_1$-$C_5$-alkoxy and $C_1$-$C_5$-alkylcarbonyl radical and it being possible for the $C_1$-$C_5$-alkoxy and $C_1$-$C_5$-carbonyl radicals to be saturated or unsaturated, branched or straight-chain and monosubstituted or polysubstituted by a radical $R^{71}$, $R^{72}$ are identical or different monovalent radicals selected from the group consisting of a hydrogen, phenyl, furyl, aryl-$C_1$-$C_5$-alkyl, $C_1$-$C_{12}$-alkyl, $C_1$-$C_{10}$-alkoxy and $C_1$-$C_{10}$-carbonyl radical, it being possible for the phenyl and furyl radicals to be unsubstituted or monosubstituted or polysubstituted by a radical $R^{73}$, where $R^{73}$ are identical or different and are selected from the group consisting of a carboxyl radical, ester or salt of the carboxyl radical, carbamoyl, phenyl, $C_1$-$C_5$-alkyl and $C_1$-$C_5$-alkoxy radical and it being possible for aryl-$C_1$-$C_5$-alkyl, $C_1$-$C_{12}$-alkyl, $C_1$-$C_{10}$-alkoxy and $C_1$-$C_{10}$-carbonyl radicals to be saturated or unsaturated, branched or straight-chain and to be monosubstituted or polysubstituted by a radical $R^{73}$.

$R^{74}$ is a divalent radical selected from the group consisting of a phenylene, furylene, aryl-$C_1$-$C_5$-alkylene, $C_1$-$C_{12}$-alkylene and $C_1$-$C_5$-alkylenedioxy radical, it being possible for the phenylene and furanylene radicals to be unsubstituted or monosubstituted or polysubstituted by a radical $R^{73}$ and it being possible for the aryl-$C_1$-$C_5$-alkylene, $C_1$-$C_{12}$-alkylene and $C_1$-$C_5$-alkylenedioxy radicals to be saturated or unsaturated, branched or straight-chain and to be monosubstituted or polysubstituted by a radical $R^{73}$, and l is 0 or 1.

Examples of the compounds of the general formulae (XXXII) to (XXXV) which can be used as mediators are:
N-hydroxy-N-methylbenzoamide,
N-hydroxy-N-methylbenzenesulfonamide,
N-hydroxy-N-methyl-p-toluenesulfonamide,
N-hydroxy-N-methylfuran-2-carboxamide,
N-hydroxy-N-methylthiophene-2-carboxamide,
N,N-dihydroxy-N,N-dimethylphthaldiamide,
N,N'-dihydroxy-N,N'-dimethylisophthaldiamide,
N,N'-dihydroxy-N,N'-dimethylterephthaldiamide,
N,N'-dihydroxy-N,N'-dimethylbenzene-1,3-disulfondiamide,
N,N'-dihydroxy-N,N'-dimethylfuran-3,4-dicarboxdiamide,
N-hydroxy-N-tert-butylbenzoamide,
N-hydroxy-N-tert-butylbenzenesulfonamide,
N-hydroxy-N-tert-butyl-p-toluenesulfonamide,
N-hydroxy-N-tert-butylfuran-2-carboxamide,
N-hydroxy-N-tert-butylthiophene-2-carboxamide,
N,N'-dihydroxy-N,N'-di-tert-butylphthaldiamide,
N,N'-dihydroxy-N,N'-di-tert-butylisophthaldiamide,
N,N'-dihydroxy-N,N'-di-tert-butylterephthaldiamide,
N,N'-dihydroxy-N,N'-di-tert-butylbenzene-1,3-disulfondiamide,
N,N'-dihydroxy-N,N'-di-tert-butylfuran-3,4-dicarboxdiamide,
N-hydroxy-N-cyclohexylbenzoamide,
N-hydroxy-N-cyclohexylbenzenesulfonamide,
N-hydroxy-N-cyclohexyl-p-toluenesulfonamide,
N-hydroxy-N-cyclohexylfuran-2-carboxamide,
N-hydroxy-N-cyclohexylthiophene-2-carboxamide,
N,N'-dihydroxy-N,N'-dicyclohexylphthaldiamide,
N,N'-dihydroxy-N,N'-dicyclohexylisophthaldiamide,
N,N'-dihydroxy-N,N'-dicyclohexylterephthaldiamide,
N,N'-dihydroxy-N,N'-dicyclohexylbenzene-1,3-disulfondiamide,
N,N'-dihydroxy-N,N'-dicyclohexylfuran-3,4-dicarboxdiamide,
N-hydroxy-N-isopropylbenzoamide,
N-hydroxy-N-isopropylbenzenesulfonamide,
N-hydroxy-N-isopropyl-p-toluenesulfonamide,
N-hydroxy-N-isopropylfuran-2-carboxamide,
N-hydroxy-N-isopropylthiophene-2-carboxamide,
N,N'-dihydroxy-N,N'-diisopropylphthaldiamide,
N,N'-dihydroxy-N,N'-diisopropylisophthaldiamide,
N,N'-dihydroxy-N,N'-diisopropylterephthaldiamide,
N,N'-dihydroxy-N,N'-diisopropylbenzene-1,3-disulfondiamide,
N,N'-dihydroxy-N,N'-diisopropylfuran-3,4-dicarboxdiamide,
N-hydroxy-N-methylacetamide,
N-hydroxy-N-tert-butylacetamide,
N-hydroxy-N-isopropylacetamide,
N-hydroxy-N-cyclohexylacetamide,
N-hydroxy-N-methylpivalamide,
N-hydroxy-N-isopropylpivalamide,
N-hydroxy-N-methylacrylamide,
N-hydroxy-N-tert-butylacrylamide,
N-hydroxy-N-isopropylacrylamide,
N-hydroxy-N-cyclohexylacrylamide,
N-hydroxy-N-methylmethanesulfonamide,
N-hydroxy-N-isopropylmethanesulfonamide,
N-hydroxy-N-isopropylmethylcarbamate,
N-hydroxy-N-methyl-3-oxobutyramide,
N,N'-dihydroxy-N,N'-dibenzoylethylenediamine,
N,N'-dihydroxy-N,N'-dimethylsuccindiamide,
N,N'-dihydroxy-N,N'-di-tert-butylmaleic acid diamide,
N-hydroxy-N-tert-butylmaleic acid monoamide,
N,N'-dihydroxy-N,N'-di-tert-butyloxaldiamide,
N,N'-dihydroxy-N,N'-di-tert-butylphosphordiamide.

Preferably used mediators from the group consisting of the N-alkyl-N-hydroxyamides are:
N-hydroxy-N-methylbenzoamide,
N-hydroxy-N-methylbenzenesulfonamide,
N-hydroxy-N-methyl-p-toluenesulfonamide,
N-hydroxy-N-methylfuran-2-carboxamide,
N,N'-dihydroxy-N,N'-dimethylphthaldiamide,
N,N'-dihydroxy-N,N'-dimethylterephthaldiamide,
N,N'-dihydroxy-N,N'-dimethylbenzene-1,3-disulfondiamide,
N-hydroxy-N-tert-butylbenzoamide,
N-hydroxy-N-tert-butylbenzenesulfonamide,
N-hydroxy-N-tert-butyl-p-toluenesulfonamide,
N-hydroxy-N-tert-butylfuran-2-carboxamide,
N,N'-dihydroxy-N,N'-di-tert-butylterephthaldiamide,
N-hydroxy-N-isopropylbenzoamide,
N-hydroxy-N-isopropyl-p-toluenesulfonamide,
N-hydroxy-N-isopropylfuran-2-carboxamide,
N,N'-dihydroxy-N,N'-diisopropylterephthaldiamide,
N,N'-dihydroxy-N,N'-diisopropylbenzene-1,3-disulfondiamide,
N-hydroxy-N-methylacetamide,
N-hydroxy-N-tert-butylacetamide,
N-hydroxy-N-isopropylacetamide,
N-hydroxy-N-cyclohexylacetamide, N-hydroxy-N-methylpivalamide,
N-hydroxy-N-tert-butylacrylamide,
N-hydroxy-N-isopropylacrylamide,
N-hydroxy-N-methyl-3-oxobutyramide,
N,N'-dihydroxy-N,N'-dibenzoylethylenediamine,
N,N'-dihydroxy-N,N'-di-tert-butylmaleic acid diamide,
N-hydroxy-N-tert-butylmaleic acid monoamide,
N,N'-dihydroxy-N,N'-di-tert-butyloxaldiamide.

The mediator may furthermore preferably be selected from the group consisting of the oximes of the general formulae (XXXVI) and (XXXVII)

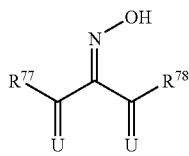

(XXXVI)

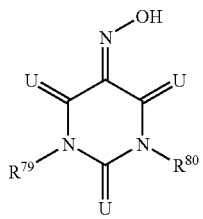

(XXXVII)

and the salts, ethers or esters thereof, in which

U are identical or different and are O, S or $NR^{75}$, where $R^{75}$ is a hydrogen, hydroxyl, formyl, carbamoyl or sulfono radical, ester or salt of the sulfono radical, sulfamoyl, nitro, amino, phenyl, aryl-$C_1$-$C_5$-alkyl, $C_1$-$C_{12}$-alkyl, $C_1$-$C_5$-alkoxy, $C_1$-$C_{10}$-carbonyl, carbonyl-$C_1$-$C_6$-alkyl, phospho, phosphono or phosphonooxy radical, ester or salt of the phosphonooxy radical, it being possible for the carbamoyl, sulfamoyl, amino and phenyl radicals to be unsubstituted or monosubstituted or polysubstituted by a radical $R^{76}$, where $R^{76}$ are identical or different and are selected from the group consisting of a hydroxyl, formyl and carboxyl radical, ester or salt of the carboxyl radical, carbamoyl and sulfono radical, ester or salt of the sulfono radical, sulfamoyl, nitro, amino, phenyl, $C_1$-$C_5$-alkyl and $C_1$-$C_5$-alkoxy radical and it being possible for the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radicals to be saturated or unsaturated, branched or straight-chain and monosubstituted or polysubstituted by a radical $R^{76}$, the radicals $R^{77}$ and $R^{78}$ are identical or different and are a halogen or carboxyl radical and ester or salt of the carboxyl radical, or have the meanings mentioned for $R^{75}$, or are linked to form a ring [—$CR^{81}R^{82}$—]$_m$, where m is 2, 3 or 4 and $R^{81}$ and $R^{82}$ are identical or different and are selected from the group consisting of a halogen and carboxyl radical, ester or salt of the carboxyl radical or have the meanings mentioned for $R^{75}$, and $R^{79}$ and $R^{80}$ have the meanings mentioned for $R^{75}$.

Particularly preferred mediators from the group consisting of the oximes are compounds of the general formula (XXXVI) in which U has the meaning of O or S and the other radicals have the abovementioned meanings. An example of such a compound is dimethyl 2-hydroxyiminomalonate.

Further particularly preferred mediators from the group consisting of the oximes are isonitroso derivatives of cyclic ureides of the general formula (XXXVII). Examples of such compounds are 1-methylvioluric acid, 1,3-dimethylvioluric acid, thiovioluric acid and alloxane-4,5-dioxime.

A further particularly preferred mediator from the group consisting of the oximes is alloxane-5-oxime hydrate (violuric acid) and/or the esters, ethers or salts thereof.

The mediator may furthermore be selected from the group consisting of vicinally nitroso-substituted aromatic alcohols of the general formulae (XXXVIII) or (XXXIX)

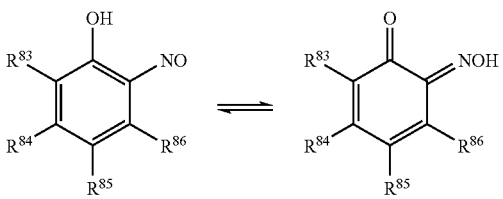

(XXXVIII)             (XXXIX)

and the salts, ethers or esters thereof, in which $R^{83}$ to $R^{86}$ are identical or different and are a hydrogen, halogen, hydroxyl, formyl, carbamoyl or carboxyl radical, ester or salt of the carboxyl radical, sulfono radical, ester or salt of the sulfono radical, sulfamoyl, nitro, nitroso, cyano, amino, phenyl, aryl-$C_1$-$C_5$-alkyl, $C_1$-$C_{10}$-alkyl, $C_1$-$C_5$-alkoxy, $C_1$-$C_{10}$-carbonyl, carbonyl-$C_1$-$C_6$-alkyl, phospho, phosphono or phosphonooxy radical, ester or salt of the phosphonooxy radical, it being possible for the carbamoyl, sulfamoyl, amino and phenyl radicals to be unsubstituted or monosubstituted or polysubstituted by a radical $R^{87}$, where $R^{87}$ are identical or different and are selected from the group consisting of a hydroxyl, formyl and carboxyl radical, ester or salt of the carboxyl radical, carbamoyl, sulfono, sulfamoyl, nitro, nitroso, amino, phenyl, $C_1$-$C_5$-alkyl and $C_1$-$C_5$-alkoxy radical, and it being possible for the aryl-$C_1$-$C_5$-alkyl, $C_1$-$C_{10}$-alkyl, $C_1$-$C_5$-alkoxy, $C_1$-$C_{10}$-carbonyl and carbonyl-$C_1$-$C_6$-alkyl radicals to be saturated or unsaturated, branched or straight-chain and to be monosubstituted or polysubstituted by a radical $R^{67}$, or the radicals $R^{83}$ to $R^{86}$ may be linked in pairs to form a ring [—$CR^{88}R^{89}$—]$_i$, where i has the abovementioned meaning, or to form a ring [—$CR^{90}$=$CR^{91}$—]$_k$, where k has the abovementioned meaning, or $R^{88}$, $R^{89}$, $R^{90}$ and $R^{91}$ being identical or different and having the meanings mentioned for $R^{83}$ to $R^{86}$.

Aromatic alcohols are preferably to be understood as meaning phenols or derivatives of phenol which have a higher degree of condensation. Preferred mediators from the group consisting of the vicinally nitroso-substituted aromatic alcohols are compounds of the general formula (XXXVIII) or (XXXIX), the synthesis of which is based on the nitrosation of substituted phenols. Examples of such compounds are:
2-nitrosophenol,
3-methyl-6-nitrosophenol,
2-methyl-6-nitrosophenol,
4-methyl-6-nitrosophenol,
3-ethyl-6-nitrosophenol,
2-ethyl-6-nitrosophenol,
4-ethyl-6-nitrosophenol,
4-isopropyl-6-nitrosophenol,
4-tert-butyl-6-nitrosophenol,
2-phenyl-6-nitrosophenol, 2-benzyl-6-nitrosophenol,
4-benzyl-6-nitrosophenol,
2-hydroxy-3-nitrosobenzyl alcohol,
2-hydroxy-3-nitrosobenzoic acid,
4-hydroxy-3-nitrosobenzoic acid,
2-methoxy-6-nitrosophenol,
3,4-dimethyl-6-nitrosophenol,
2,4-dimethyl-6-nitrosophenol,
3,5-dimethyl-6-nitrosophenol,
2,5-dimethyl-6-nitrosophenol,
2-nitrosoresorcinol,
4-nitrosoresorcinol,
2-nitrosoorcinol,
2-nitrosophloroglucinol,
4-nitrosopyrogallol,
4-nitroso-3-hydroxyaniline and
4-nitro-2-nitrosophenol.

Further preferred mediators from the group consisting of the vicinally nitroso-substituted aromatic alcohols are o-nitroso derivatives of aromatic alcohols having a higher degree of condensation. Examples of such compounds are
2-nitroso-1-naphthol,
1-methyl-3-nitroso-2-naphthol and
9-hydroxy-10-nitrosophenanthrene.

The mediator can furthermore preferably be selected from the group consisting of the hydroxypyridine, aminopyridine, hydroxyquinoline, aminoquinoline, hydroxyisoquinoline and aminoisoquinoline derivatives having nitroso or mercapto substituents in the ortho or para position relative to the hydroxyl or amino groups, tautomers of said compounds and the salts, ethers and esters thereof. Preferred mediators from said group are compounds of the general formula (XL), (XLI) or (XLII)

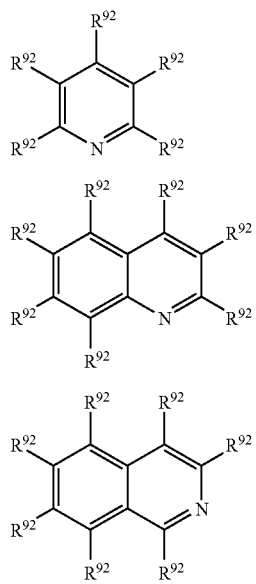

and tautomers, salts, ethers or esters of said compounds, in the formulae (XL), (XLI) or (XLII) two radicals $R^{92}$ ortho or para relative to one another being a hydroxyl and nitroso radical or hydroxyl and mercapto radical or nitroso and amino radical, the remaining radicals $R^{92}$ being identical or different and being selected from the group consisting of the hydrogen, halogen, hydroxyl, mercapto, formyl, cyano, carbamoyl and carboxyl radical, ester and salt of the carboxyl radical, sulfono radical, ester and salt of the sulfono radical, sulfamoyl, nitro, nitroso, amino, phenyl, aryl-$C_1$-$C_5$-alkyl, $C_1$-$C_{12}$-alkyl, $C_1$-$C_5$-alkoxy, $C_1$-$C_{10}$-carbonyl, carbonyl-$C_1$-$C_6$-alkyl, phospho, phosphono and phosphonooxy radical, ester and salt of the phosphonooxy radical, it being possible for the carbamoyl, sulfamoyl, amino, mercapto and phenyl radicals to be unsubstituted or monosubstituted or polysubstituted by a radical $R^{93}$, where $R^{93}$ are identical or different and are selected from the group consisting of a hydroxyl, formyl, cyano and carboxyl radical, ester or salt of the carboxyl radical, carbamoyl, sulfono, sulfamoyl, nitro, nitroso, amino, phenyl, $C_1$-$C_5$-alkyl and $C_1$-$C_5$-alkoxy radical or $C_1$-$C_5$-alkylcarbonyl radical, and it being possible for the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radicals to be saturated or unsaturated, branched or straight-chain and to be monosubstituted or polysubstituted by a radical $R^{73}$, and it being possible for two radicals $R^{92}$ or two radicals $R^{93}$ each or $R^{92}$ and $R^{93}$ to be linked in pairs via a bridge [—$CR^{94}R^{95}$—]$_i$, where i has the abovementioned meaning, it being possible for one or more nonneighboring groups —$CR^{94}R^{95}$— to be replaced by oxygen, sulfur or an optionally $C_1$-$C_5$-alkyl-substituted imino radical, and it being possible for two neighboring groups —$CR^{94}R^{95}$— to be replaced by a group [—$CR^{94}$=$CR^{95}$—], $R^{94}$ and $R^{95}$ being identical or different and being a hydrogen or carboxyl radical, ester or salt of the carboxyl radical, phenyl, $C_1$-$C_5$-alkyl or $C_1$-$C_5$-alkoxy radical or $C_1$-$C_5$-alkylcarbonyl radical.

Particularly preferred mediators are compounds of the general formula (XL) or (XLI) and the tautomers, salts, ethers or esters thereof, in the formulae (XL) and (XLI) two radicals $R^{92}$ in ortho position relative to one another particularly preferably being hydroxyl and nitroso radical or hydroxyl and mercapto radical or nitroso radical and amino radical and the remaining radicals $R^{92}$ being identical or different and being selected from the group consisting of the hydrogen, hydroxyl, mercapto, formyl, carbamoyl and carboxyl radical, ester and salt of the carboxyl radical, sulfono radical, ester and salt of the sulfono radical, sulfamoyl, nitro, nitroso, amino, phenyl, aryl-$C_1$-$C_5$-alkyl, $C_1$-$C_5$-alkyl, $C_1$-$C_5$-alkoxy, $C_1$-$C_5$-carbonyl, carbonyl-$C_1$-$C_6$-alkyl, phospho, phosphono and phosphonooxy radical, ester and salt of the phosphonooxy radical, it being possible for the carbamoyl, sulfamoyl, amino, mercapto and phenyl radicals to be unsubstituted or monosubstituted or polysubstituted by a radical $R^{93}$ and it being possible for the aryl-$C_1$-$C_5$-alkyl, $C_1$-$C_5$-alkyl, $C_1$-$C_5$-alkoxy, $C_1$-$C_5$-carbonyl and carbonyl-$C_1$-$C_6$-alkyl radicals to be saturated or unsaturated, branched or straight-chain and to be monosubstituted or polysubstituted by a radical $R^{93}$, $R^{93}$ having the abovementioned meanings and it being possible for the two radicals $R^{93}$ each to be linked in pairs via a bridge [—$CR^{94}R^{95}$—]$_i$ where i has the abovementioned meaning, and $R^{94}$ and $R^{95}$ having the abovementioned meanings and it being possible for one or more nonneighboring groups —$CR^{94}R^{95}$— to be replaced by oxygen or an optionally $C_1$-$C_5$-alkyl-substituted imino radical.

Examples of compounds of the general formula (XL), (XLI) or (XLII) which can be used as a mediator are:
2,6-dihydroxy-3-nitrosopyridine,
2,3-dihydroxy-4-nitrosopyridine,
2,6-dihydroxy-3-nitrosopyridine-4-carboxylic acid,
2,4-dihydroxy-3-nitrosopyridine,
3-hydroxy-3-mercaptopyridine,
2-hydroxy-3-mercaptopyridine,
2,6-diamino-3-nitrosopyridine, 2,6-diamino-3-nitrosopyridine-4-carboxylic acid,
2-hydroxy-3-nitrosopyridine,
3-hydroxy-2-nitrosopyridine,
2-mercapto-3-nitrosopyridine,
3-mercapto-2-nitrosopyridine,
2-amino-3-nitrosopyridine,
3-amino-2-nitrosopyridine,
2,4-dihydroxy-3-nitrosoquinoline,
8-hydroxy-5-nitrosoquinoline,
2,3-dihydroxy-4-nitrosoquinoline,
3-hydroxy-4-nitrosoisoquinoline,
4-hydroxy-3-nitrosoisoquinoline,
8-hydroxy-5-nitrosoisoquinoline and tautomers of these compounds.

Preferred mediators of the general formula (XL), (XLI) or (XLII) are
2,6-dihydroxy-3-nitrosopyridine,
2,6-diamino-3-nitrosopyridine,
2,6-dihydroxy-3-nitrosopyridine-4-carboxylic acid,
2,4-dihydroxy-3-nitrosopyridine,
2-hydroxy-3-mercaptopyridine,
2-mercapto-3-pyridinol,
2,4-dihydroxy-3-nitrosoquinoline,
8-hydroxy-5-nitrosoquinoline,
2,3-dihydroxy-4-nitrosoquinoline and tautomers of these compounds.

Very particularly preferred mediators are
2,2,6,6-tetramethylpiperidin-1-oxyl (TEMPO),
4-hydroxy-2,2,6,6-tetramethylpiperidin-1-oxyl,
4-amino-2,2,6,6-tetramethylpiperidin-1-oxyl,
4-acetoxy-2,2,6,6-tetramethylpiperidin-1-oxyl,
4-benzoyloxy-2,2,6,6-tetramethylpiperidin-1-oxyl,
PIPO (polymer immobilized piperidinyloxyl),
N-hydroxyphthalimide,
1-hydroxy-1H-benzotriazole,
violuric acid,
N-hydroxyacetanilide and the abovementioned derivatives thereof.

Most preferred are
2,2,6,6-tetramethylpiperidin-1-oxyl (TEMPO),
4-hydroxy-2,2,6,6-tetramethylpiperidin-1-oxyl,
4-amino-2,2,6,6-tetramethylpiperidin-1-oxyl,
4-acetoxy-2,2,6,6-tetramethylpiperidin-1-oxyl,
4-benzoyloxy-2,2,6,6-tetramethylpiperidin-1-oxyl,
PIPO (polymer immobilized by piperidinyloxyl),
3-amino-N-hydroxyphthalimide,
4-amino-N-hydroxyphthalimide,
N-hydroxyphthalimide,
3-hydroxy-N-hydroxyphthalimide,
3-methoxy-N-hydroxyphthalimide,
3,4-dimethoxy-N-hydroxyphthalimide,
4,5-dimethoxy-N-hydroxyphthalimide,
3,6-dihydroxy-N-hydroxyphthalimide,
3,6-dimethoxy-N-hydroxyphthalimide,
3-methyl-N-hydroxyphthalimide,
4-methyl-N-hydroxyphthalimide,
3,4-dimethyl-N-hydroxyphthalimide,
3,5-dimethyl-N-hydroxyphthalimide,
3,6-dimethyl-N-hydroxyphthalimide,
3-isopropyl-6-methyl-N-hydroxyphthalimide,
3-nitro-N-hydroxyphthalimide,
4-nitro-N-hydroxyphthalimide,
1-hydroxy-1H-benzotriazole,
violuric acid,
N-hydroxyacetanilide,
3-nitrosoquinoline-2,4-diol,
2,4-dihydroxy-3-nitrosopyridine,
2,6-dihydroxy-3-nitrosopyridine,
2,4-dinitroso-1,3-dihydroxybenzene,
2-nitroso-1-naphthol-4-sulfonic acid and
1-nitroso-2-naphthol-3,6-disulfonic acid.

In the method according to the invention, the mediator is preferably used in amounts of from 0.01 to 100 mol %, more preferably from 0.1 to 20 mol %, most preferably from 0.1 to 5 mol %, based on the molar amount of the carbinol groups present in the organosilicon compounds used.

The method according to the invention can be carried out with one or more mediators described, preferably with one or two mediators, more preferably with one mediator. The mediator can be dissolved in an organic or aqueous phase or used in supported form as an independent phase.

In the method according to the invention, the corresponding, active oxoammonium species is produced in situ by the oxidizing agent and is not isolated. In a particular embodiment, however, the mediator can also be converted into the active oxoammonium species in a separate, preceding oxidation reaction, isolated and used in an equimolar amount, based on the carbinol groups present in the organosilicon compounds used.

Preferably used oxidizing agents are air, oxygen, hydrogen peroxide, organic peroxides, perborates or persulfates, organic or inorganic peracids, salts and derivatives of the peracids, chlorine, bromine, iodine, hypohalic acids and the salts thereof, for example in the form of bleaching liquor, halic acids and the salts thereof, halogen acids and the salts thereof, $Fe(CN)_6^{3-}$ and N-chloro compounds. However, oxidizing agents may also be metal oxides or anodes of electrolysis cells. Furthermore, the oxidizing agent used may also be produced in situ, for example electrochemically, by hydrolysis, such as, for example, by hydrolysis with N-chloro compounds, or by redox reactions, such as by disproportionation of chlorine or bromine in alkaline solution, for example in the case of hypochlorite or hypobromite solutions, or such as, for example, in the redox reaction between hypochlorite and bromide, which leads to the formation of hypobromite.

In the case of salt-like oxidizing agents, sodium, potassium, calcium, ammonium or tetraalkylammonium are preferred as opposite ions.

The oxidizing agent can be used individually or as a mixture, optionally in each case in combination with enzymes.

In the context of the invention, the term enzyme also includes enzymatically active proteins or peptides or prosthetic groups of enzymes. Enzymes which may be used in the multicomponent system according to the invention are preferably oxidoreductases of the classes 1.1.1 to 1.97 according to international enzyme nomenclature, Committee of the International Union of Biochemistry and Molecular Biology (Enzyme Nomenclature, Academic Press, Inc., 1992, pages 24-154).

Preferably used enzymes are those of the classes mentioned below:

enzymes of class 1.1, which include all dehydrogenases which act on primary and secondary alcohols and semiacetals and which have $NAD^+$ or $NADP^+$ (subclass 1.1.1), cytochromes (1.1.2), oxygen ($O_2$) (1.1.3), disulfides (1.1.4), quinones (1.1.5) as acceptors or which have other acceptors (1.1.99).

Particularly preferred from this class are the enzymes of class 1.1.5 having quinones as acceptors and the enzymes of class 1.1.3 having oxygen as an acceptor.

Particularly preferred in this class is cellobiose: quinone-1-oxidoreductase (1.1.5.1).

Enzymes of class 1.2 are furthermore preferred. This enzyme class includes those enzymes which oxidize the aldehydes to the corresponding acids or oxo groups. The acceptors may be $NAD^+$, $NADP^+$ (1.2.1), cytochromes (1.2.2), oxygen (1.2.3), sulfides (1.2.4), iron-sulfur proteins (1.2.5) or other acceptors (1.2.99).

Particularly preferred here are the enzymes of group (1.2.3) having oxygen as an acceptor.

Enzymes of class 1.3 are furthermore preferred. This class includes enzymes which act on CH—CH groups of the donor. The corresponding acceptors are $NAD^+$ and $NADP^+$ (1.3.1), cytochromes (1.3.2), oxygen (1.3.3), quinones or related compounds (1.3.5), iron-sulfur proteins (1.3.7) or other acceptors (1.3.99).

Bilirubin oxidase (1.3.3.5) is particularly preferred. Also particularly preferred here are the enzymes of class (1.3.3) having oxygen as an acceptor and (1.3.5) having quinones, etc. as an acceptor.

Enzymes of class 1.4 which act on CH—$NH_2$ groups of the donor are furthermore preferred. The corresponding acceptors are $NAD^+$, $NADP^+$ (1.4.1), cytochromes (1.4.2), oxygen (1.4.3), disulfides (1.4.4), iron-sulfur proteins (1.4.7) or other acceptors (1.4.99).

Enzymes of class 1.4.3 having oxygen as an acceptor are also particularly preferred here.

Enzymes of class 1.5 which act on CH—NH groups of the donor are furthermore preferred. The corresponding acceptors are $NAD^+$, $NADP^+$ (1.5.1), oxygen (1.5.3), disulfides (1.5.4), quinones (1.5.5) or other acceptors (1.5.99).

Enzymes having oxygen (1.5.3) and having quinones (1.5.5) as acceptors are also particularly preferred here.

Enzymes of class 1.6 which act on NADH or NADPH are furthermore preferred. The acceptors here are $NADP^+$ (1.6.1), hemoproteins (1.6.2), disulfides (1.6.4), quinones (1.6.5), $NO_2$ groups (1.6.6) and a flavin (1.6.8) or some other acceptors (1.6.99).

Enzymes of class 1.6.5 having quinones as acceptors are particularly preferred here.

Enzymes of class 1.7 which act on other $NO_2$ compounds as donors and have cytochromes (1.7.2), oxygen ($O_2$) (1.7.3), iron-sulfur proteins (1.7.7) or others (1.7.99) as acceptors are furthermore preferred.

The class 1.7.3 having oxygen as an acceptor is particularly preferred here.

Enzymes of class 1.8 which act on sulfur groups as donors and have $NAD^+$ and $NADP^+$ (1.8.1), cytochromes (1.8.2), oxygen (1.8.3), disulfides (1.8.4), quinones (1.8.5), iron-sulfur proteins (1.8.7) or others (1.8.99) as acceptors are furthermore preferred.

The class 1.8.3 having oxygen ($O_2$) and (1.8.5) having quinones as acceptors is particularly preferred.

Enzymes of class 1.9 which act on the heme groups as donors and have oxygen ($O_2$) (1.9.3), $NO_2$ compounds (1.9.6) and others (1.9.99) as acceptors are furthermore preferred.

The group 1.9.3 having oxygen ($O_2$) as an acceptor (cytochrome oxidases) is particularly preferred here.

Enzymes of class 1.12 which act on hydrogen as a donor are furthermore preferred. The acceptors are $NAD^+$ or $NADP^+$ (1.12.1) or others (1.12.99).

Enzymes of class 1.13 and 1.14 (oxygenases) are furthermore preferred.

Enzymes the class 1.15 which act on superoxide radicals as acceptors are furthermore preferred. Superoxide dismutase (1.15.1.1) is particularly preferred here.

Enzymes of class 1.16 are furthermore preferred. $NAD^+$ or $NADP^+$ (1.16.1) or oxygen ($O_2$) (1.16.3) act as acceptors.

Enzymes of class 1.16.3.1 (ferroxidase, e.g. ceruloplasmin) are particularly preferred here.

Further preferred enzymes are those which belong to the group 1.17 (action on $CH_2$ groups, which are oxidized to —CHOH—), 1.18 (action on reduced ferredoxin as a donor), 1.19 (action on reduced flavodoxin as a donor), and 1.97 (other oxidoreductases).

The enzymes of group 1.11 which act on a peroxide as an acceptor are furthermore particularly preferred. This single subclass (1.11.1) contains the peroxidases.

The cytochrome-C-peroxidases (1.11.1.5), catalase (1.11.1.6), peroxydase (1.11.1.7), iodide peroxidase (1.11.1.8), glutathione peroxidase (1.11.1.9), chloride peroxidase (1.11.1.10), L-ascorbate peroxidase (1.11.1.11), phospholipid hydroperoxide glutathione peroxidase (1.11.1.12), manganese peroxidase (1.12.1.13), diarylpropane peroxidase (ligninase, lignin peroxidase) (1.11.1.14) are particularly preferred here.

Enzymes of class 1.10 which act on biphenols and related compounds are very particularly preferred. They catalyze the oxidation of biphenols and ascorbates. $NAD^+$, $NADP^+$ (1.10.1), cytochromes (1.10.2), oxygen (1.10.3) or others (1.10.99) act as acceptors.

Among these in turn, enzymes of class 1.10.3 having oxygen ($O_2$) as an acceptor are particularly preferred. Among the enzymes of this class, the enzymes catechol oxidase (tyrosinase) (1.10.3.1), L-ascorbate oxidase (1.10.3.3), o-aminophenol oxidase (1.10.3.4) and laccase (benzenediol: oxygen oxidoreductase) (1.10.3.2) are preferred, the laccases (benzenediol: oxygen oxidoreductase) (1.10.3.2) being particularly preferred.

Said enzymes are commercially available or can be obtained by standard methods. Suitable organisms for the production of the enzymes are, for example, plants, animal cells, bacteria and fungi. In principle, both naturally occurring organisms and organisms modified by genetic engineering can be enzyme producers. Parts of monocellular or polycellular organisms are also conceivable as enzyme producers, especially cell cultures. Further particularly preferred enzymes, such as those of group 1.11.1, but especially 1.10.3 and in particular for the production of laccases, for example, white rot fungi, such as Pleurotus, Phlebia and Trametes, are used.

The oxidizing agents used are preferably employed in concentrations of from 0.1 M to their respective saturation concentration.

If the oxidizing agents used in the method according to the invention are 2-electron oxidizing agents they are preferably used in amounts of from 0.1 to 125 mol %, more preferably from 50 to 110 mol %, and most preferably from 75 to 105 mol %, based on the molar amount of the carbinol groups present in the organosilicon compounds used. If the oxidizing agents used in the method according to the invention are 1-electron oxidizing agents, they are preferably used in amounts of from 0.2 to 250 mol %, more preferably from 100 to 220 mol %, and most preferably from 150 to 210 mol %, based on the molar amount of the carbinol groups present in the organosilicon compounds used. They are preferably 2-electron oxidizing agents.

Among the metal oxides used as oxidizing agents, those having a solubility of less than 1 g/l in the reaction medium are preferred. Bismuth(III) oxide, iridium(III) oxide, cerium (IV) oxide, cobalt(II) oxide, cobalt(III) oxide, iron(III) oxide, manganese(IV) oxide, tin(IV) oxide, niobium(V) oxide, antimony(V) oxide, indium(III) oxide, mercury(II) oxide, lead (IV) oxide, silver(I) oxide, copper(II) oxide and palladium(II) oxide are preferred.

Lead(IV) oxide, manganese(IV) oxide, silver(I) oxide, copper(II) oxide and palladium(II) oxide are particularly preferred.

The electrodes of the electrolysis cells used for the oxidation may be identical or different. They preferably consist of carbon, iron, lead, lead dioxide, copper, nickel, zinc, cadmium, mercury, tantalum, titanium, silver, platinum, platinized platinum, palladium, rhodium, gold or alloys of said compounds.

Stainless steels, tantalum, titanium, rhodium, platinum or gold are particularly preferred. Most preferably, the electrodes consist of stainless steel, stainless steels of the group 1.4xxx (according to DIN 17850) in turn being preferred.

The electrodes may optionally have been coated with other substances by deposition, sputtering, galvanization or similar methods. The surface area of the electrodes may have been increased by suitable methods, for example by grinding, polishing, sandblasting, etching or erosion.

Further possible additives are halogens, e.g. bromine, or salts, e.g. alkali metal, alkaline earth metal or ammonium halides or sulfates, carbonates or bicarbonates, phosphoric acid and the alkali metal, alkaline earth metal or ammonium salts thereof or carbon dioxide. These additives can be added to the oxidizing agent or to the phase containing the oxidizing agent or to the organosilicon compound having carbinol groups to be oxidized or to the phase containing the organosilicon compound having carbinol groups to be oxidized, optionally in dissolved form, or can be fed to the reaction mixture optionally in dissolved form as further component.

In the oxidation with hypochlorite, for example, the addition of bromine or bromide in amounts of from 0.01 to 100 mol %, based on the amount of hypochlorite used, is preferred. The addition of bromine or bromide in amounts of from 1 to 50 mol % is particularly preferred.

The method according to the invention can be carried out in a homogeneous 1-phase or in a 2-phase or multiphase system, the 2-phase reaction system being preferred.

A particularly preferred embodiment employs a 2-phase reaction system consisting of a liquid organosilicon-containing phase, which contains the organosilicon compound which is to be oxidized and has carbinol groups and optionally one or more organic solvents, and a liquid organosilicon-free phase containing the oxidizing agent.

The liquid organosilicon-free phase containing the oxidizing agent is preferably an aqueous phase. The pH of the aqueous phase is preferably from 4 to 14, more preferably from 6 to 12. The desired pH is preferably established by adding a buffer, e.g. sodium bicarbonate, disodium hydroxide phosphate or sodium dihydrogen phosphate or a buffer mixture or an acid, e.g. carbon dioxide, phosphoric acid, hydrochloric acid or sulfuric acid, or a base, e.g. NaOH.

In a preferred embodiment, the method according to the invention can be carried out as a 2-phase reaction system both with and without additional solvents, the procedure without additional solvents being preferred.

Suitable additional solvents are polar or nonpolar solvents and any desired mixtures of these solvents with one another or with water. Linear or branched saturated or unsaturated aliphatic hydrocarbons having 1-20 carbon atoms, cyclic saturated or unsaturated aliphatic hydrocarbons having 5-20 carbon atoms or aromatic hydrocarbons having 5-20 carbon atoms may be mentioned by way of example as suitable organic solvents, it being possible for one or more hydrogen atom(s) or one or more carbon atom(s) to be replaced by heteroatoms.

The additional solvents are preferably linear or branched, saturated or unsaturated aliphatic hydrocarbons having 1 to 16 carbon atoms, cyclic saturated or unsaturated aliphatic hydrocarbons having 5-16 carbon atoms, or aromatic hydrocarbons having 6-16 carbon atoms, it being possible for one or more hydrogen atom(s), independently of one another, to be replaced by F, Cl, Br, $NO_2$ or CN, it being possible for one or more $CH_2$ group(s), independently of one another, to be replaced by O, NH, C=O, S, S=O, $SO_2$ or P=O, and it being possible for one or more CH group(s), independently of one another, to be replaced by N or P, or for quaternary carbon atoms to be replaced by Si.

Examples of suitable organic solvents are hexane, petroleum ether, cyclohexane, decalin, methylene chloride, chloroform, carbon tetrachloride, 1,2-dichloroethane, chlorobenzene, benzene, toluene, 1-chloronaphthalene, ethylene carbonate, $CO_2$, methyl acetate, ethyl acetate, butyl acetate, acetonitrile, acetamide, tetrahydro-1,3-dimethyl-2(1H)-pyrimidinone (DMPU), hexamethylphosphorotriamide (HMPT), dimethyl sulfoxide (DMSO), sulfolane, diethyl ether, methyl tert-butyl ether, ethylene glycol dimethyl ether, ethylene glycol diethyl ether, diethylene glycol diethyl ether, tetrahydrofuran, dioxane, acetone, diisopropyl ketone and polydimethylsiloxanes.

The organosilicon compound which is to be oxidized and has carbinol groups can be used in concentrations of from 0.1 to 100% by weight, based on the organic solution, preferably from 1 to 50% by weight.

If the method according to the invention is carried out in a 2-phase reaction system, thorough mixing of the two reaction phases for creating a large internal reaction surface area is necessary for a quantitative conversion of the carbinol groups. The thorough mixing of the phases can be produced either by turbulent flow or in principle by means of all known mixing systems, for example static mixing elements or mixing nozzles, stirrers, ultrasound, electrical, magnetic or electromagnetic fields, etc., or by combinations thereof. An overview of the most important embodiment is given, for example, in "Ullmann's Encyclopedia of Industrial Chemistry" (Vol. B2, $5^{th}$ edition, VCH Weinheim, 1988, pages 24-1 to 25-13 and 25-19 to 25-21; Vol. B4, $5^{th}$ edition, VCH Weinheim, 1992, pages 561 to 586).

The method according to the invention is preferably carried out in a 2-phase reaction system so that an average particle size of less than or equal to 200 µm is present in the continuous phase.

In the inventive method, the reactions are preferably carried out at temperatures of from −100 to +150° C., more preferably from −50 to +100° C., and in particular from −20 to +50° C. The reaction times are preferably from 0.1 seconds to 72 hours, preferably from 1 second to 24 hours, more preferably from 1 second to 10 hours and most preferably from 1 second to 5 hours.

The method according to the invention can be carried out batchwise, semicontinuously or completely continuously in reactor systems suitable for this purpose, such as, for example, a batch reactor, batch reactor cascade, loop reactor, flow tube, tubular reactor, microreactor, centrifugal pumps and any desired combinations thereof. An overview of the most important embodiments is given, for example, in "Ullmann's Encyclopedia of Industrial Chemistry" (Vol. B4, $5^{th}$ edition, VCH Weinheim, 1992, pages 87-120). The reaction is preferably carried out continuously in a 2-phase reaction system.

The method according to the invention has a number of advantages over the prior art. It is comparatively simple, can be realized without special complicated apparatuses and, owing to the low reaction temperature and the catalytic use of the mediators used, is economical and protects resources.

Because of the selective and virtually quantitative oxidation of the carbinol groups, even polymeric polyorganosiloxanes and organosiloxane resins give outstanding reaction yields which are substantially above the yields of the methods described in the prior art. Furthermore, scarcely any by-products are formed and the reaction products can be isolated cleanly and in a simple manner. In addition, the relatively mild reaction conditions permit the use of the method according to the invention also in the case of organosilicon compounds having sensitive substituents. The method can be operated continuously and optionally even without additional organic solvents, which means a further advantage with regard to cost, space-time yield and lasting environmental compatibility.

If desired, the organosilicon compounds obtained by the method according to the invention can be further modified.

If the organosilicon compounds prepared according to the invention are compounds of the formula (I) where a+b+c+d=4, i.e. silanes, they can, depending on the type of substituent X, be alkoxylated in a manner known to the person skilled in the art (X is a chlorine atom), hydrolyzed or (co)condensed to give organopolysiloxanes (X is a chlorine atom or hydroxyl, methoxy or ethoxy radical), or cocondensed with linear organopolysiloxanes having terminal hydroxyl groups and with organosiloxane resins containing silanol groups (X is a chlorine atom or hydroxyl, methoxy or ethoxy radical).

If the organosilicon compounds prepared according to the invention are compounds of the formula (I) where a+b+c+d≦3, i.e. organosiloxanes, they can be equilibrated in a manner known to the person skilled in the art with further organopolysiloxanes, preferably selected from the group consisting of linear organopolysiloxanes having terminal triorganosilyloxy groups, linear organopolysiloxanes having terminal hydroxyl groups, cyclic organopolysiloxanes and copolymers comprising diorganosiloxane and monoorganosiloxane units, or with organosiloxane resins containing silanol groups, permitting, for example, the establishment of the desired molecular weight and the targeted distribution of the carbonyl groups in the molecule and optionally the introduction of further functionalities.

Preferably used linear organopolysiloxanes having terminal hydroxyl groups are those of the formula

  (XLIII), preferably used linear organopolysilanes having terminal triorganosilyloxy groups are those of the formula

  (XLIV), preferably used cyclic organopolysiloxanes are those of the formula

  (XLV), preferably used copolymers are those comprising units of the formula

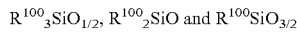

and preferably used organosiloxane resins containing silanol groups are those comprising units of the formula $[R^{100}_3SiO_{1/2}]$ and $[SiO_{4/2}]$, these also containing additional Si-bonded OH groups, in which $R^{100}$ in each case may be identical or different and have a meaning stated for R, p is 0 or an integer from 1 to 2000, q is 0 or an integer from 1 to 2000 and r is an integer from 3 to 12.

The ratio of the organopolysiloxanes used in the optionally performed cocondensation or equilibration and organosilicon compounds prepared according to the invention are determined only by the desired proportion of carbonyl groups in the organosilicon compound produced in the optionally performed cocondensation or equilibration and by the desired average chain length.

The optionally subsequently performed alkoxylation, hydrolysis, condensation, cocondensation or equilibration reactions are carried out in a manner known to the person skilled in the art.

Organosilicon compounds having carbonyl radicals are distinguished firstly by a high reactivity compared with nucleophiles and—as a result of this—broad reaction spectrum and secondly by the sensitivity to redox processes which is typical of carbonyl groups. The possible applications of organosilicon compounds having carbonyl radicals are accordingly extensive.

Owing to the high reactivity of the carbonyl groups with O-, N- and S-nucleophiles, organosilicon compounds having carbonyl groups are outstandingly suitable, for example, for the permanent treatment of appropriate materials, such as, for example, of natural fibers (such as wool, silk, cotton, keratin fibers), cellulose and cellulose fibers and the blended fabrics thereof with manmade fibers, such as polypropylene, polyester or polyamide fibers. Typical target effects are, for example, soft, fluid handle, improved elasticity, antistatic properties, low frictional values, surface smoothness, gloss, crease recovery, color fastnesses, resistance to washing, hydrophilicity, tear propagation strength, reduced tendency to pilling, easy-care and soil-release properties, improved comfort during wearing, high resistance of the treatment to washing and care processes, improved industrial processability, for example with regard to processing and production rate.

Furthermore, organosilicon compounds having carbonyl radicals are suitable as auxiliary in the tanning and finishing of leather and for the sizing and surface finishing of paper. Organosilicon compounds having carbonyl radicals can also be used as additives in coatings and finishes, where, for example, they lead to a reduction in the surface roughness and hence to a reduction in the sliding resistance of the finish.

Other potential applications are the use of organosilicon compounds having carbonyl radicals as an additive in cosmetic formulations, for example in skin-care compositions, as conditioners in hair-washing compositions or for the reversible anchoring of fragrances in the polymer matrix for achieving slow-release properties, as building protection compositions and as surface-active agents, such as, for example, detergents, surfactants, emulsifiers, antifoams and foam stabilizers.

In addition, organosilicon compounds having carbonyl radicals can be used as free radical transfer agents for controlling free radical polymerization processes, as a chemical building block, such as, for example, for the production of plastics or resins and as an intermediate for further syntheses. Thus, the aldehyde and ketone groups can be further modified as desired by methods known to the person skilled in the art, such as, for example, by (hemi)acetalization, oxidation, reduction, reaction with amines to give imines and Schiff's bases, oxime, hydrazone and semicarbazone formation, reaction with CH-acidic compounds or use as a CH-acidic reaction component.

The following method examples explain the invention.

Example 1

121 g of a 3-hydroxypropyldimethylsilyl-terminated polydimethylsiloxane having an OH content of 3.2% in 400 ml of methylene chloride, 1.90 g (11 mmol) of 4-hydroxy-TEMPO, 50 ml of saturated sodium bicarbonate solution and 2.27 g (22 mmol) of sodium bromide were cooled to −10° C., and 177 g of industrial bleaching liquor (content about 1.8 M; a pH 9.5 was established by adding 2 N sulfuric acid) were added with vigorous stirring by means of an anchor stirrer (2000 rpm; RZR stirrer from Heidolph) and thorough cooling in the course of 200 s. A suspension-like white mixture, in which the silicone oil droplets having an average particle size of from about 100 to 150 μm were dispersed in the continuous aqueous phase, formed during this procedure. After about 5 mm, the phases were separated and the organic phase containing the product was analyzed by NMR spectroscopy. Yield (standard analysis): 96% of Si-bonded 2-formylethyl groups, 4% of unreacted hydroxypropyl groups.

Example 1A

Effect of Larger Particle Size On Yield

Example 1 was repeated in an analogous manner, except that a magnetic stirrer (IKAMAG® RCT from IKA Labortechnik) with cylindrical magnetic stirring rod (L: 25 mm) was used instead of the anchor stirrer or propeller stirrer and stirring was effected at 1000 rpm. The resulting dispersion is substantially more coarse-particled and has an average particle size of the silicone oil droplets of more than 500 μm. After the product phase was separated off, the organic phase was analyzed by NMR spectroscopy. Yield (standard analysis): 46% of Si-bonded 2-formylethyl groups, 54% of unreacted hydroxypropyl groups.

Example 2

121 g of a 3-hydroxypropyldimethylsilyl-terminated polydimethylsiloxane having an OH content of 1.25%, 950 mg (5.5 mmol) of 4-hydroxy-TEMPO, 50 ml of saturated sodium bicarbonate solution and 1135 mg (11 mmol) of sodium bromide were cooled to −10° C. and 77 g of industrial bleaching liquor (content about 1.9 M; pH 9.5 established by adding 2 N sulfuric acid) were added rapidly with vigorous stirring and thorough cooling. After about 15 mm the phases were separated and the organic phase containing the product was analyzed by NMR spectroscopy. Yield (standard analysis): 95% of Si-bonded 2-formylethyl groups, 5% of unreacted hydroxypropyl groups.

Example 3

The reaction was repeated analogously to Example 2 with 100 g of the polydimethylsiloxanes specified further in Table 1, functionalized with 3-hydroxypropyl side groups and having trimethylsilyl terminal groups, the amounts of 4-hydroxy-TEMPO, saturated $NaHCO_3$ solution, sodium bromide and bleaching liquor stated in the table being used. At the end of the reaction, the reaction mixture is neutralized with 10% strength HCl (aq.) (pH=6-7). After the organosilicon phase has been separated off, all volatile constituents have been removed in vacuo and filtration has been effected, polydimethylsiloxane functionalized with formylethyl side groups and having trimethylsilyl terminal groups is obtained as a virtually colorless, clear oil.

TABLE 1

| | Example | | |
|---|---|---|---|
| | 3a | 3b | 3c |
| OH content [%] | 1.34 | 0.85 | 0.6 |
| 4-OH-Tempo [g] | 0.8 | 0.5 | 0.375 |
| $NaHCO_3$ solution [ml] | 45 | 30 | 20 |
| NaBr [g] | 1.0 | 0.6 | 0.45 |
| Reaction time [min] | 15 | 25 | 35 |
| Yield | 98.2 | 96.4 | 95.5 |

Example 4

Analogously to Examples 3, 100 g of a linear polydimethylsiloxane having—as further specified in Table 2—side or terminal carbinol groups (carbinol oil) were reacted to give the corresponding formyl-functionalized polydimethylsiloxanes.

TABLE 2

| Carbinol oil | Substituent | Type of substituent | OH content [%] |
|---|---|---|---|
| A | polyoxyalkylene radical $-C_3H_6-(C_2H_4O)_6-(C_4H_8O)_{14}H$ | side group | 0.7 |
| B | polyoxyalkylene radical $-C_3H_6-(C_2H_4O)_{20}-(C_4H_8O)_{20}H$ | side group | 0.48 |
| C | 3-[2-ethyl-3-hydroxy-3-(hydroxymethyl)propoxy]propyl | alpha, omega-terminal groups | 1.55 |
| D | 4-hydroxy-2-methylbutyl | side group | 0.44 |
| E | 3-hydroxypropyl | monofunctional | 1.02 |

Table 3 illustrates the conditions of the synthesis.

TABLE 3

| | Example | | | | |
|---|---|---|---|---|---|
| | 4a | 4b | 4c | 4d | 4e |
| Carbinol oil | A | B | C | D | E |
| Additional solvent | — | toluene | — | — | ethyl acetate |
| 4-OH-Tempo [g] | 0.44 | 0.30 | 0.98 | 0.275 | 0.33 |
| $NaHCO_3$ solution [ml] | 25 | 15 | 52 | 15 | 18 |
| NaBr [g] | 0.52 | 0.36 | 1.17 | 0.33 | 0.39 |
| Reaction time [min] | 30 | 45 | 12 | 35 | 10 |
| Yield | 96.3 | 97.6 | 92.4 | 98.1 | 95.9 |

Example 5

The following solutions were prepared:

Solution 1: 430 mg (2.5 mmol, 1.0 mol %) of 4-hydroxy-TEMPO were dissolved in 1000 g of 3-hydroxypropyl-dimethylsilyl-terminated polydimethylsiloxane having an OH content of 0.5 mmol per g.

Solution 2: 2 l of sodium hypochlorite solution (industrial bleaching liquor) were adjusted to a pH of 9.5 with about 80 ml of 20 percent sulfuric acid. Content about 1.9 M.

Solution 3: 84.9 g of NaBr in 313 ml of water.

By means of metering pumps, the solutions 1, 2 and 3 were pumped from reservoirs by means of a static mixing element synchronously into a 20 m long titanium tube (internal diameter 3 mm, external diameter 4.1 mm) wound into a spiral. The pumping rate was 400 ml/min for solution 1 and 130 ml/min for solution 2 and 0.5 l/h for solution 3. The reaction mixture was collected in a container and optionally diluted with ethyl acetate. The organic phase was separated off. After removal of all volatile constituents in vacuo and filtration the polydimethylsiloxane functionalized by terminal formylethyl groups was obtained as a virtually colorless, clear oil. Yield: 90% of silicone oil having Si-bonded 2-formylethyl groups (quantitative NMR analysis).

Example 6

Further oxidations in the batch mode were carried out with the 3-hydroxypropyldimethylsilyl-terminated polydimethylsiloxane used in Example 5. For reagents used, experimental conditions and yields, cf. Table 4.

particle size of 200 μm or less, wherein the organosilicon compounds having carbinol radicals are those of the formula $$A'_v R_{3-v} SiO(SiR_2O)_n SiRA'O)_o SiR_{3-v} A'_v \quad (I'')$$

in which

A' are identical or different radicals of the formula

(II)

R are identical or different and are a monovalent, linear or cyclic, branched or straight-chain optionally substituted hydrocarbon radical,

TABLE 4

| Catalyst/cocatalyst (mol %)* | Oxidizing agent (mol %)* | Reaction medium | Reaction temperature (° C.) | Duration of reaction | Yield (%) |
|---|---|---|---|---|---|
| 4-Hydroxy-TEMPO (1), KBr (1) | NaOCl (120) | ethyl acetate/water | 20 | 5 min | 95 |
| 4-Hydroxy-TEMPO (2.5), KBr (1) | NaOCl (120) | without organic solvent | 10 to 25 | 3 min | 92 |
| 4-Acetamido-TEMPO (2) | NaOBr (110) | toluene/water | 10 | 2 min | 97 |
| TEMPO (0.1) | N-chloro-succinimide (1.1) | $CH_2Cl_2$ | 5 | 20 min | 98 |
| TEMPO (1) | PhI(OAc)$_2$ (110) | $CH_2Cl_2$ | 20 | 2 h | 80 |
| TEMPO (1) | KHSO$_5$ (110) | $CH_2Cl_2$ | 20 | 5.5 h | 75 |
| TEMPO (1), Bu$_4$N$^+$Br$^-$ (2) | oxone (200) | $CH_2Cl_2$ | 20 | 1.2 h | 70 |
| TEMPO (1) | m-chloro-perbenzoic acid | $CH_2Cl_2$ | 5 | 35 min | 75 |
| 4-Hydroxy-TEMPO (5), CuCl (10) | $O_2$ | DMF | 25 | 3 h | 90 |
| TEMPO (10), laccase (1000 ncat./g siloxane) | $O_2$ | acetonitrile/ 0.1 M NaOAc (pH 5.0) | 38 | 2 d | 70 |
| TEMPO (10), laccase (1000 ncat./g siloxane) | $O_2$ | THF/ 0.1 M NaOAc (pH 5.1) | 39 | 3 d | 71 |
| TEMPO (10), laccase (500 ncat./g siloxane) | $O_2$ | without organic solvent | 40 | 2 d | 65 |
| TEMPO (2.5), RuCl$_2$(PPh$_3$)$_3$ (2.5) | $O_2$ | without organic solvent | 100 | 5 h | 90 |

*based on the molar amount of carbinol groups present

The invention claimed is:

1. A process for producing organosilicon compounds containing carbonyl radicals by oxidation of organosilicon compounds containing carbinol radicals with the aid of a mediator selected from the group consisting of the aliphatic, cycloaliphatic, heterocyclic and aromatic NO—, NOH— and

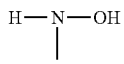

group-containing compounds and mixtures thereof, and an oxidizing agent, wherein when the process takes place as a mixture, the organosilicon compound containing carbinol groups is present in a dispersed phase with a v is 0, 1, 2 or 3, n is 0 or an integer from 1 to 2000, o is 0 or an integer from 1 to 2000, with the proviso that at least one radical A' is present, wherein $Y^1$ is a divalent or polyvalent, linear or cyclic, branched or straight-chain organic radical optionally substituted and/or interrupted by the atoms N, O, P, B, Si or S; $Y^2$ is a hydrogen atom or a monovalent, linear or cyclic, branched or straight-chain, organic radical optionally substituted and/or interrupted by the atoms N, O, P, B, Si or S; and y, depending on the valency of radical $Y^1$ is $\geq 2$.

2. The process of claim 1, wherein at least one nitroxyl radical of the formulae

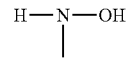

(XI)

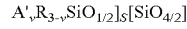

(XII)

is used as a mediator,
in which

R$^{16}$ are identical or different and are phenyl, aryl-$C_1$-$C_5$-alkyl, $C_1$-$C_{12}$-alkyl, $C_1$-$C_5$-alkoxy, $C_1$-$C_{10}$-carbonyl or carbonyl-$C_1$-$C_6$-alkyl radicals, the phenyl radicals being unsubstituted, monosubstituted, or polysubstituted by a radical R$^{18}$ and the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radicals being saturated or unsaturated, branched or straight-chain and optionally monosubstituted or polysubstituted by a radical R$^{18}$, the optional radical R$^{18}$ being present once or several times, each R$^{18}$ independently being a hydroxyl, formyl or carboxyl radical, ester or salt of a carboxyl radical, carbamoyl, sulfono, sulfamoyl, nitro, nitroso, amino, phenyl, benzoyl, $C_1$-$C_5$-alkyl or $C_1$-$C_5$-alkoxy radical or a $C_1$-$C_5$-alkyl-carbonyl radical, R$^{17}$ are independently a hydrogen atom or a hydroxyl, mercapto, formyl, cyano, carbamoyl or carboxyl radical, ester or salt of the carboxyl radical, sulfono radical, ester or salt of the sulfono radical, a sulfamoyl, nitro, nitroso, amino, phenyl, aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radical, phospho, phosphono or phosphonooxy radical, ester or salt of the phosphonooxy radical, the carbamoyl, sulfamoyl, amino, mercapto and phenyl radicals optionally monosubstituted or polysubstituted by a radical R$^{12}$, and the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radical being saturated or unsaturated, straight-chain or branched and optionally monosubstituted or polysubstituted by a radical R$^{12}$; and wherein a [—CR$^{17}$R$^{17}$—] group is optionally replaced by oxygen, an optionally $C_1$-$C_5$-alkyl-substituted imino radical, a (hydroxy)imino radical, a carbonyl group, or a vinylidene group optionally monosubstituted or disubstituted by R$^{12}$, and wherein two neighboring groups [—CR$^{17}$R$^{17}$—] are optionally replaced by a group [—CR$^{17}$=CR$^{17}$—], [—CR$^{17}$=] or [—CR$^{17}$=N(O)—], and R$^{12}$ is optionally present once or several times and R$^{12}$ being identical or different and being a hydroxyl, formyl, cyano or carboxyl radical, ester or salt of the carboxyl radical, carbamoyl, sulfono, sulfamoyl, nitro, nitroso, amino, phenyl, $C_1$-$C_5$-alkyl, $C_1$-$C_5$-alkoxy or $C_1$-$C_5$-alkylcarbonyl radical.

3. The process of claim 2, wherein the nitroxyl radicals of the formulae (XI) and (XII) are linked to a polymeric structure by bonding to one or more radicals R$^{17}$.

4. The process of claim 1, wherein at least one mediator is selected from the group consisting of
2,2,6,6-tetramethylpiperidin-1-oxyl (TEMPO),
4-hydroxy-2,2,6,6-tetramethylpiperidin-1-oxyl,
4-amino-2,2,6, 6-tetramethylpiperidin-1-oxyl,
4-acetoxy-2,2, 6,6-tetramethylpiperidin-1-oxyl,
4-benzoyloxy-2,2,6, 6-tetramethylpiperidin-1-oxyl and
PIPO (polymer immobilized piperidinyloxyl).

5. The process of claim 1, wherein the mediator is present in an amount of from 0.01 to 100 mol %, based on the amount of carbinol groups present in the organosilicon compound.

6. The process of claim 1, wherein the oxidizing agent is selected from the group consisting of air, oxygen, hydrogen peroxide, organic peroxides, perborates, persulfates, organic and inorganic peracids, salts and derivatives of the peracids, chlorine, bromine, iodine, hypohalic acids and the salts thereof optionally in the form of bleaching liquor, halic acids and the salts thereof, halogen acids and the salts thereof, Fe(CN)$_6^{3-}$ and N-chloro compounds, and mixtures thereof, the oxidizing agents optionally used in combination with one or more enzymes.

7. The process of claim 1, wherein the oxidizing agent is a 2-electron oxidizing agent and is used in an amount of from 0.1 to 125 mol %, based on the amount of carbinol groups present in the organosilicon compounds.

8. The process of claim 1, wherein the oxidizing agent is a metal oxide or an anode of an electrolysis cell.

9. The process of claim 1, which is carried out continuously.

10. A process for producing organosilicon compounds containing carbonyl radicals by oxidation of organosilicon compounds containing carbinol radicals with the aid of a mediator selected from the group consisting of the aliphatic, cycloaliphatic, heterocyclic and aromatic NO—, NOH— and $$H-N-OH$$

group-containing compounds and mixtures thereof, and an oxidizing agent, wherein when the process takes place as a mixture, the organosilicon compound containing carbinol groups is present in a dispersed phase with a particle size of 200 μm or less, wherein organosilicon compounds having carbinol radicals are those of the formula $$A'_vR_{3-v}SiO_{1/2}]_s[SiO_{4/2}]  \quad (I''')$$

in which
A' are identical or different radicals of the formula

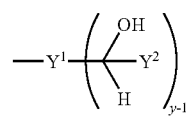

(II)

R are identical or different and are a monovalent, linear or cyclic, branched or straight-chain optionally substituted hydrocarbon radical,
v is 0, 1, 2 or 3
s has a value of from 0.2 to 6, and describes the number of M units [A'$_v$R$_{3-v}$SiO$_{1/2}$] per Q unit [SiO$_{4/2}$],
with the proviso that at least one radical A' is present, wherein Y$^1$ is a divalent or polyvalent, linear or cyclic, branched or straight-chain organic radical optionally substituted and/or interrupted by the atoms N, O, P, B, Si or S; $Y^2$ is a hydrogen atom or a monovalent, linear or cyclic, branched or straight-chain, organic radical optionally substituted and/or interrupted by the atoms N, O, P, B, Si or S; and y, depending on the valency of radical $Y^1$ is $\geq 2$.

11. The process of claim 10, wherein at least one nitroxyl radical of the formulae

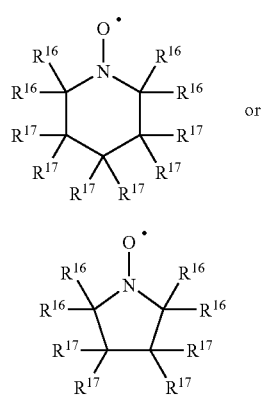

is used as a mediator,
in which
$R^{16}$ are identical or different and are phenyl, aryl-$C_1$-$C_5$-alkyl, $C_1$-$C_{12}$-alkyl, $C_1$-$C_5$-alkoxy, $C_1$-$C_{10}$-carbonyl or carbonyl-$C_1$-$C_6$-alkyl radicals, the phenyl radicals being unsubstituted, monosubstituted, or polysubstituted by a radical $R^{18}$ and the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radicals being saturated or unsaturated, branched or straight-chain and optionally monosubstituted or polysubstituted by a radical $R^{18}$, the optional radical $R^{18}$ being present once or several times, each $R^{18}$ independently being a hydroxyl, formyl or carboxyl radical, ester or salt of a carboxyl radical, carbamoyl, sulfono, sulfamoyl, nitro, nitroso, amino, phenyl, benzoyl, $C_1$-$C_5$-alkyl or $C_1$-$C_5$-alkoxy radical or a $C_1$-$C_5$-alkylcarbonyl radical,
$R^{17}$ are independently a hydrogen atom or a hydroxyl, mercapto, formyl, cyano, carbamoyl or carboxyl radical, ester or salt of the carboxyl radical, sulfono radical, ester or salt of the sulfono radical, a sulfamoyl, nitro, nitroso, amino, phenyl, aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radical, phospho, phosphono or phosphonooxy radical, ester or salt of the phosphonooxy radical, the carbamoyl, sulfamoyl, amino, mercapto and phenyl radicals optionally monosubstituted or polysubstituted by a radical $R^{12}$, and the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radical being saturated or unsaturated, straight-chain or branched and optionally monosubstituted or polysubstituted by a radical $R^{12}$; and wherein a [—$CR^{17}R^{17}$—] group is optionally replaced by oxygen, an optionally $C_1$-$C_5$-alkyl-substituted imino radical, a (hydroxy) imino radical, a carbonyl group, or a vinylidene group optionally monosubstituted or disubstituted by $R^{12}$, and wherein two neighboring groups [—$CR^{17}R^{17}$—] are optionally replaced by a group [—$CR^{17}$=$CR^{17}$—], [—$CR^{17}$=] or [—$CR^{17}$=N(O)—], and $R^{12}$ is optionally present once or several times and $R^{12}$ being identical or different and being a hydroxyl, formyl, cyano or carboxyl radical, ester or salt of the carboxyl radical, carbamoyl, sulfono, sulfamoyl, nitro, nitroso, amino, phenyl, $C_1$-$C_5$-alkyl, $C_1$-$C_5$-alkoxy or $C_1$-$C_5$-alkylcarbonyl radical.

12. The process of claim 10, wherein at least one mediator is selected from the group consisting of
2,2,6,6-tetramethylpiperidin-1-oxyl (TEMPO),
4-hydroxy-2,2, 6,6-tetramethylpiperidin-1-oxyl,
4-amino-2,2, 6,6-tetramethylpiperidin-1-oxyl,
4-acetoxy-2,2,6,6-tetramethylpiperidin-1-oxyl,
4-benzoyloxy-2,2,6,6-tetramethylpiperidin-1-oxyl and
PIPO (polymer immobilized piperidinyloxyl).

13. The process of claim 10, wherein the mediator is present in an amount of from 0.01 to 100 mol %, based on the amount of carbinol groups present in the organosilicon compound.

14. A process for producing organosilicon compounds containing carbonyl radicals by oxidation of organosilicon compounds containing carbinol radicals with the aid of a mediator selected from the group consisting of the aliphatic, cycloaliphatic, heterocyclic and aromatic NO—, NOH— and

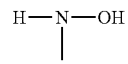

group-containing compounds and mixtures thereof, and an oxidizing agent, wherein when the process takes place as a mixture, the organosilicon compound containing carbinol groups is present in a dispersed phase with a particle size of 200 μm or less,
wherein organosilicon compounds having carbonyl radicals which are obtained are those of the formula

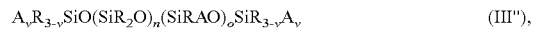

in which
A are identical or different and are a radical of the formula

R are identical or different and are a monovalent, linear or cyclic, branched or straight-chain optionally substituted hydrocarbon radical,
v is 0, 1, 2 or 3,
n is 0 or an integer from 1 to 2000,
o is 0 or an integer from 1 to 2000,
with the proviso that at least one radical A is present, wherein $Y^1$ is a divalent or polyvalent, linear or cyclic, branched or straight-chain organic radical optionally substituted and/or interrupted by the atoms N, O, P, B, Si or S; $Y^3$ is a hydrogen atom or a monovalent, linear or cyclic, branched or straight-chain organic radical optionally substituted and/or be interrupted by the atoms N, O, P, B, Si or S; and y, depending on the valency of radical $Y^1$ is $\geq 2$.

15. The process of claim 14, wherein at least one nitroxyl radical of the formulae

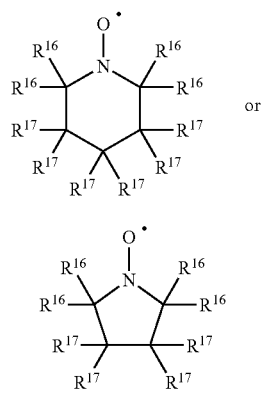

is used as a mediator,
in which
- $R^{16}$ are identical or different and are phenyl, aryl-$C_1$-$C_5$-alkyl, $C_1$-$C_{12}$-alkyl, $C_1$-$C_5$-alkoxy, $C_1$-$C_{10}$-carbonyl or carbonyl-$C_1$-$C_6$-alkyl radicals, the phenyl radicals being unsubstituted, monosubstituted, or polysubstituted by a radical $R^{18}$ and the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radicals being saturated or unsaturated, branched or straight-chain and optionally monosubstituted or polysubstituted by a radical $R^{18}$, the optional radical $R^{18}$ being present once or several times, each $R^{18}$ independently being a hydroxyl, formyl or carboxyl radical, ester or salt of a carboxyl radical, carbamoyl, sulfono, sulfamoyl, nitro, nitroso, amino, phenyl, benzoyl, $C_1$-$C_5$-alkyl or $C_1$-$C_5$-alkoxy radical or a $C_1$-$C_5$-alkyl-carbonyl radical,
- $R^{17}$ are independently a hydrogen atom or a hydroxyl, mercapto, formyl, cyano, carbamoyl or carboxyl radical, ester or salt of the carboxyl radical, sulfono radical, ester or salt of the sulfono radical, a sulfamoyl, nitro, nitroso, amino, phenyl, aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radical, phospho, phosphono or phosphonooxy radical, ester or salt of the phosphonooxy radical, the carbamoyl, sulfamoyl, amino, mercapto and phenyl radicals optionally monosubstituted or polysubstituted by a radical $R^{12}$, and the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radical being saturated or unsaturated, straight-chain or branched and optionally monosubstituted or polysubstituted by a radical $R^{12}$; and wherein a [—$CR^{17}R^{17}$—] group is optionally replaced by oxygen, an optionally $C_1$-$C_5$-alkyl-substituted imino radical, a (hydroxy)imino radical, a carbonyl group, or a vinylidene group optionally monosubstituted or disubstituted by $R^{12}$, and wherein two neighboring groups [—$CR^{17}R^{17}$—] are optionally replaced by a group [—$CR^{17}$=$CR^{17}$—], [—$CR^{17}$=] or [—$CR^{17}$=N(O)—], and $R^{12}$ is optionally present once or several times and $R^{12}$ being identical or different and being a hydroxyl, formyl, cyano or carboxyl radical, ester or salt of the carboxyl radical, carbamoyl, sulfono, sulfamoyl, nitro, nitroso, amino, phenyl, $C_1$-$C_5$-alkyl, $C_1$-$C_5$-alkoxy or $C_1$-$C_5$-alkylcarbonyl radical.

16. The process of claim 14, wherein at least one mediator is selected from the group consisting of 2,2,6,6-tetramethylpiperidin-1-oxyl (TEMPO),
4-hydroxy-2,2,6,6-tetramethylpiperidin-1-oxyl,
4-amino-2,2,6,6-tetramethylpiperidin-1-oxyl,
4-acetoxy-2,2,6,6-tetramethylpiperidin-1-oxyl,
4-benzoyloxy-2,2,6,6-tetramethylpiperidin-1-oxyl and
PIPO (polymer immobilized piperidinyloxyl).

17. The process of claim 14, wherein the mediator is present in an amount of from 0.01 to 100 mol %, based on the amount of carbinol groups present in the organosilicon compound.

18. A process for producing organosilicon compounds containing carbonyl radicals by oxidation of organosilicon compounds containing carbinol radicals with the aid of a mediator selected from the group consisting of the aliphatic, cycloaliphatic, heterocyclic and aromatic NO—, NOH— and

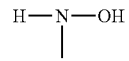

group-containing compounds and mixtures thereof, and an oxidizing agent, wherein when the process takes place as a mixture, the organosilicon compound containing carbinol groups is present in a dispersed phase with a particle size of 200 µm or less, wherein organosilicon compounds having carbonyl radicals which are obtained are those of the formula $$[A_vR_{3-v}SiO_{1/2}]_s[SiO_{4/2}] \qquad (III''')$$

in which
A are identical or different and are a radical of the formula

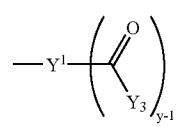

R are identical or different and are a monovalent, linear or cyclic, branched or straight-chain optionally substituted hydrocarbon radical,
v is 0, 1, 2 or 3,
s may assume a value from 0.2 to 6, and describes the number of M units $[A_vR_{3-v}SiO_{1/2}]$ per Q unit $[SiO_{4/2}]$,
with the proviso that at least one radical A is present, wherein $Y^1$ is a divalent or polyvalent, linear or cyclic, branched or straight-chain organic radical optionally substituted and/or interrupted by the atoms N, O, P, B, Si or S; $Y^3$ is a hydrogen atom or a monovalent, linear or cyclic, branched or straight-chain organic radical optionally substituted and/or be interrupted by the atoms N, O, P, B, Si or S; and y, depending on the valency of radical $Y^1$ is $\geq 2$.

19. The process of claim 18, wherein at least one nitroxyl radical of the formulae

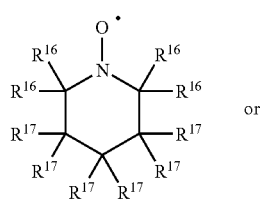

-continued

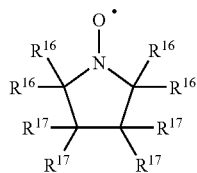

(XII)

is used as a mediator,
in which
$R^{16}$ are identical or different and are phenyl, aryl-$C_1$-$C_5$-alkyl, $C_1$-$C_{12}$-alkyl, $C_1$-$C_5$-alkoxy, $C_1$-$C_{10}$-carbonyl or carbonyl-$C_1$-$C_6$-alkyl radicals, the phenyl radicals being unsubstituted, monosubstituted, or polysubstituted by a radical $R^{18}$ and the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radicals being saturated or unsaturated, branched or straight-chain and optionally monosubstituted or polysubstituted by a radical $R^{18}$, the optional radical $R^{18}$ being present once or several times, each $R^{18}$ independently being a hydroxyl, formyl or carboxyl radical, ester or salt of a carboxyl radical, carbamoyl, sulfono, sulfamoyl, nitro, nitroso, amino, phenyl, benzoyl, $C_1$-$C_5$-alkyl or $C_1$-$C_5$-alkoxy radical or a $C_1$-$C_5$-alkylcarbonyl radical, $R^{17}$ are independently a hydrogen atom or a hydroxyl, mercapto, formyl, cyano, carbamoyl or carboxyl radical, ester or salt of the carboxyl radical, sulfono radical, ester or salt of the sulfono radical, a sulfamoyl, nitro, nitroso, amino, phenyl, aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radical, phospho, phosphono or phosphonooxy radical, ester or salt of the phosphonooxy radical, the carbamoyl, sulfamoyl, amino, mercapto and phenyl radicals optionally monosubstituted or polysubstituted by a radical $R^{12}$, and the aryl-$C_1$-$C_5$-alkyl, $C_1$-$C_{12}$-alkyl, $C_1$-$C_5$-alkoxy, $C_1$-$C_{10}$-carbonyl and carbonyl-$C_1$-$C_6$-alkyl radical being saturated or unsaturated, straight-chain or branched and optionally monosubstituted or polysubstituted by a radical $R^{12}$; and wherein a [—$CR^{17}R^{17}$—] group is optionally replaced by oxygen, an optionally $C_1$-$C_5$-alkyl-substituted imino radical, a (hydroxy) imino radical, a carbonyl group, or a vinylidene group optionally monosubstituted or disubstituted by $R^{12}$, and wherein two neighboring groups [—$CR^{17}R^{17}$—] are optionally replaced by a group [—$CR^{17}$=$CR^{17}$—], [—$CR^{17}$=] or [—$CR^{17}$=N(O)—], and $R^{12}$ is optionally present once or several times and $R^{12}$ being identical or different and being a hydroxyl, formyl, cyano or carboxyl radical, ester or salt of the carboxyl radical, carbamoyl, sulfono, sulfamoyl, nitro, nitroso, amino, phenyl, $C_1$-$C_5$-alkyl, $C_1$-$C_5$-alkoxy or $C_1$-$C_5$-alkylcarbonyl radical.

20. The process of claim 18, wherein at least one mediator is selected from the group consisting of
2,2,6,6-tetramethylpiperidin-1-oxyl (TEMPO),
4-hydroxy-2,2,6,6-tetramethylpiperidin-1-oxyl,
4-amino-2,2,6,6-tetramethylpiperidin-1-oxyl,
4-acetoxy-2,2,6,6-tetramethylpiperidin-1-oxyl,
4-benzoyloxy-2,2,6,6-tetramethylpiperidin-1-oxyl and
PIPO (polymer immobilized piperidinyloxyl).

21. The process of claim 18, wherein the mediator is present in an amount of from 0.01 to 100 mol %, based on the amount of carbinol groups present in the organosilicon compound.

* * * * *